(12) United States Patent
Tasiemski et al.

(10) Patent No.: US 8,173,768 B2
(45) Date of Patent: May 8, 2012

(54) PEPTIDES HAVING ANTIMICROBIAL AND NEUROTROPHIC ACTIVITY AND USES THEREOF

(75) Inventors: Aurélie Tasiemski, La Madeleine (FR); Michel Salzet, Bourghelles (FR)

(73) Assignees: Centre National de la Recherche Scientifique, Paris (FR); Universite des Sciences et Technologies de Lille, Villeneuve d'Ascq (FR)

( * ) Notice: Subject to any disclaimer, the term of this patent is extended or adjusted under 35 U.S.C. 154(b) by 200 days.

(21) Appl. No.: 12/501,687

(22) Filed: Jul. 13, 2009

(65) Prior Publication Data

US 2011/0009329 A1    Jan. 13, 2011

(51) Int. Cl.
| | |
|---|---|
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 14/475 | (2006.01) |
| C07K 14/48 | (2006.01) |
| A61K 38/18 | (2006.01) |
| A61K 38/17 | (2006.01) |
| A61K 38/00 | (2006.01) |

(52) U.S. Cl. ........... 530/300; 514/7.6; 514/8.3; 514/8.4; 514/2.2; 530/324

(58) Field of Classification Search ................ None
See application file for complete search history.

(56) References Cited

U.S. PATENT DOCUMENTS

| | | | | |
|---|---|---|---|---|
| 7,435,792 | B2 * | 10/2008 | Coen et al. ............... | 530/350 |
| 7,923,216 | B2 * | 4/2011 | Roux et al. ............... | 435/7.8 |
| 2010/0136034 | A1 * | 6/2010 | Guichard et al. ........ | 424/184.1 |
| 2011/0002914 | A1 * | 1/2011 | Coen et al. .............. | 424/130.1 |

OTHER PUBLICATIONS

Tasiemski, A., "Antimicrobial Peptides in Annelids", ISJ 5, 2008, pp. 75-82.
Schikorski, D. et al.,"Microbial Challenge Promotes the Regenerative Process of the Injured Central Nervous System of the Medicinal Leech by Inducing the Synthesis of Antimicrobial Peptides in Neurons and Microglia", The Journal of Immunology, 2008, pp. 1083-1095, vol. 181.

* cited by examiner

*Primary Examiner* — Chang-Yu Wang
(74) *Attorney, Agent, or Firm* — Young & Thompson

(57) ABSTRACT

A method for preventing a break out of a neurodegenerative disease in an individual and for treating an individual suffering from a neurodegenerative disease comprising the administration of an effective amount of an antimicrobial and neurotrophic peptide.

3 Claims, 11 Drawing Sheets

Figure 2:
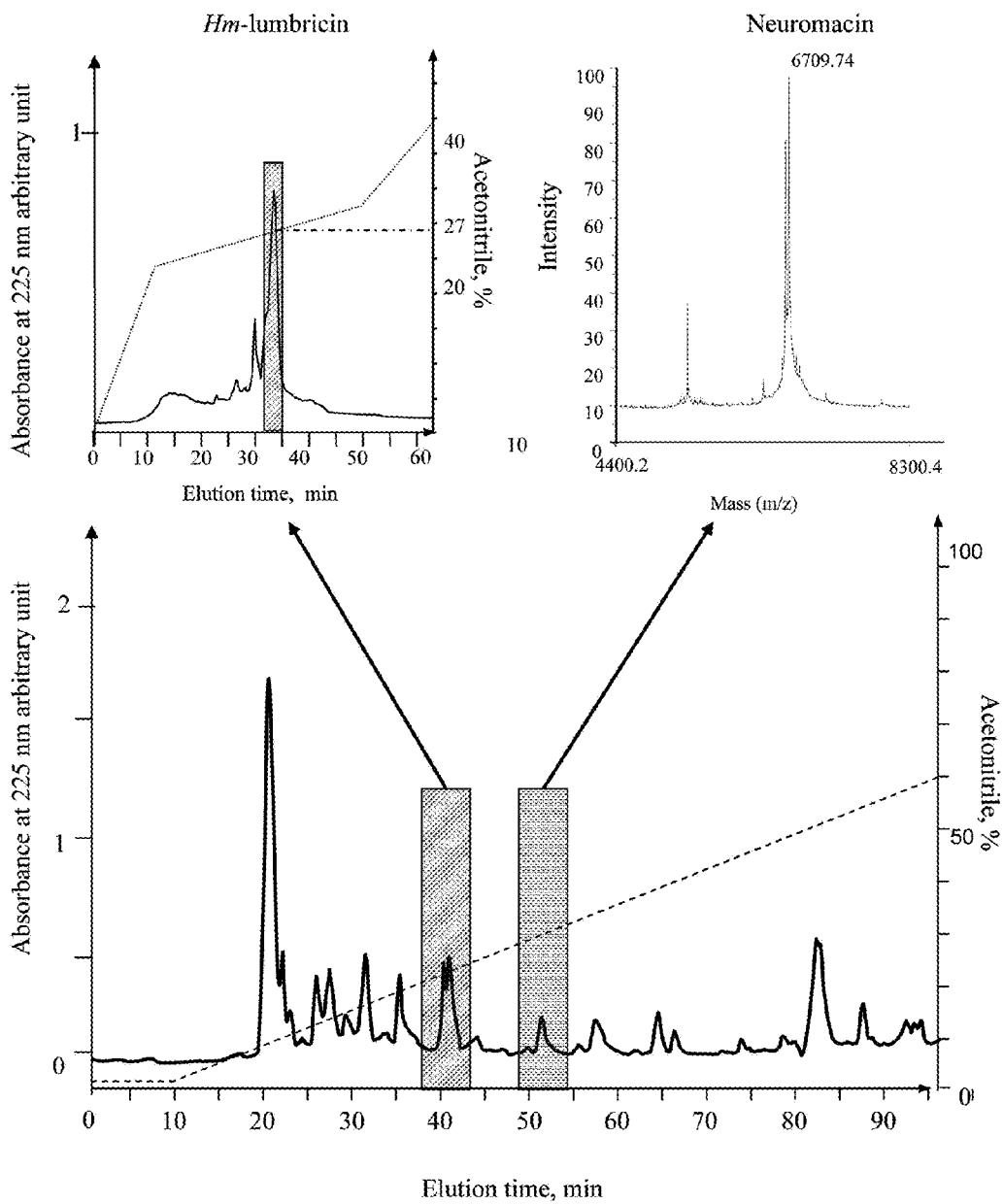

Figure 1
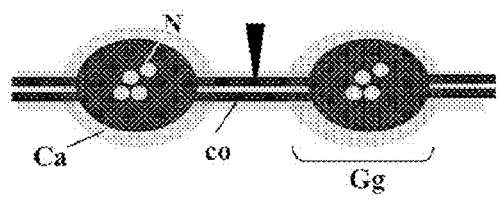
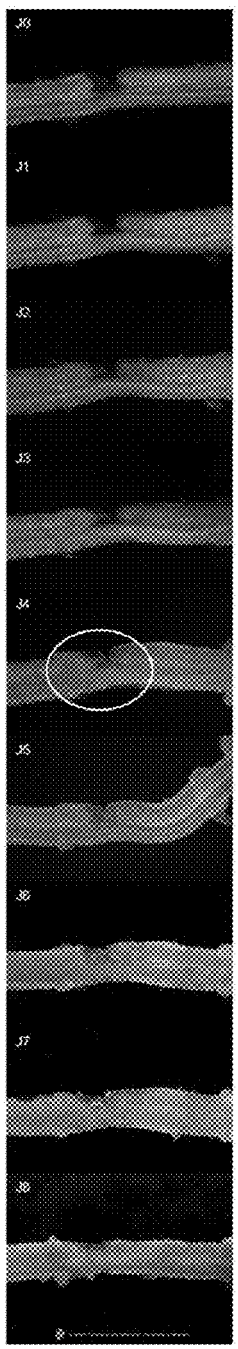
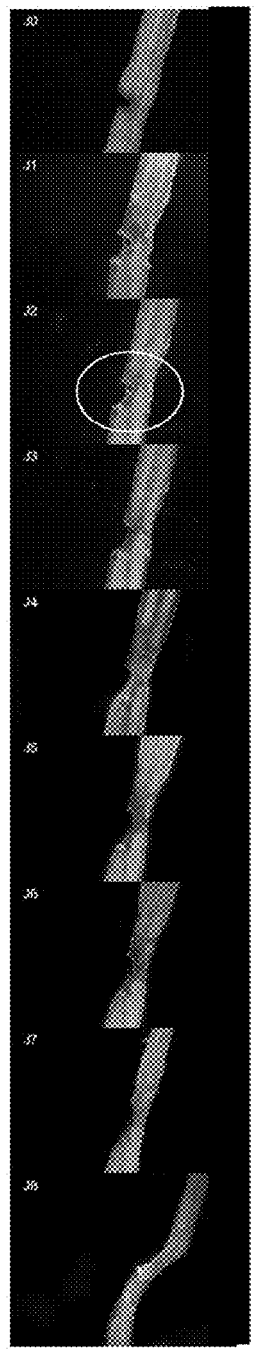
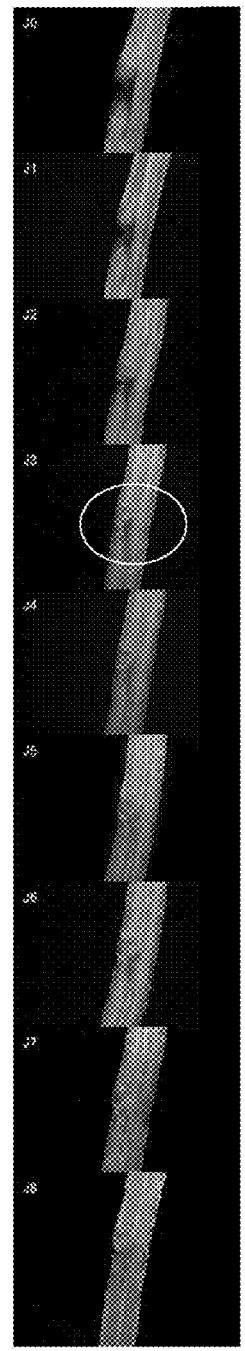

Figure 3

A

```
atg gctcttctcaacaagttgctctgctttgctctggtcttcatgatcttcggtgagttc
    M  A  L  L  N  K  L  L  C  F  A  L  V  F  M  I  F  G  E  F
gtgactccggattgctacgaggactggagcaggtgcacgcctggaacgtcattcctgact
 V  T  P  D  C  Y  E  D  W  S  R  C  T  P  G  T  S  F  L  T
ggaatcctgtggaaagattgccacagccgttgcaaggaactcggtcacaggggaggacga
 G  I  L  W  K  D  C  H  S  R  C  K  E  L  G  H  R  G  G  R
tgtgtggattcaccaagcaaacactgccctggagtcctcaagaacaacaaacagtgtcat
 C  V  D  S  P  S  K  H  C  P  G  V  L  K  N  N  K  Q  C  H
tgctac tga tctgaagaattgttgaaatatgttggagattctggaaggacagtgaccatg
 C  Y
atttgtgatttctttaaaaatcacttagttaagtaaaaacattggcgatgattacgctt
acataaataaagtattattttgcgattgcaccattccaaaaaaaaaaaaaaaaaaaaaa
```

B

```
atg tcagcaagtacgagaggcaaaaggacaaaagaagttacggtgaaaggttcagcatg
    M  S  K  Y  E  R  Q  K  D  K  R  S  Y  G  E  R  F  S  M
ttcacaggccctcagttcatttcgcccccgagaggatcaaacccaacaaaattctccag
 F  T  G  P  Q  F  I  S  P  P  E  R  I  K  P  N  K  I  L  Q
tgggatggggaggcatgcccatttacgccacgtcggggctgcagccgac taa gagag
 W  D  G  E  G  M  P  I  Y  A  T  S  G  A  A  A  E
ccgattggcgactgaccagccaatatgaccaggcaatgacaagccaggatattttggag
taattcgacattcagagacggtccttaaaatgtctccaatgatttgtggaatcgattcga
gttttgaattaaacgatatctcaataaaatatcggttaaattttcaatttcgtcacca
aatattaatgtcaaataaatagttctttctaaagcgaaaaaaaaaaaaaaaaa
```

FIGURE 4

A

*T.tessulatum* AY434032 ----------------
GCFEDWSRCSPSTSRGTGVLWRDCDSYCKVCFKADRG-ECFDSP 43
*H.medicinalis* EU164975 ----------------
GCFEDWSRCSPSTASATGVLWRSCDSYCKVCFKADRG-ECYDSP 43
*L.rubellus* DR008243 -----------------GCYEDWSRCTPSTSWLTGILWKSCTNRCKE-
-QGHRGGNCRDSP 42
Neuromacin EU156754 ----------------
DCYEDWSRCTPGTSFLTGILWKDC<u>H</u>SRCKE--LG<u>H</u>RGGRCVDSP 42
*B.glabrata* CK989857 ------------
NVIGRCWDTWSRCSTWSRWFTGRVWLTRDGKCRE--LGKRGGNCVMTP 46
*A.californica* DQ489547
MDKKAANGGKEKGPLEACWDEWSRCTGWSSAGTGVLWKSCDDQCKK--
LGKSGGECVLTP 58
                                    \* \*\*\*\*   \*\* \*\*   \*    \*      \* \*

*T.tessulatum* AY434032       SLNCPQR-LPNNKQCRCINARTAKDNRNPTCWA 75
(SEQ ID NO 37)
*H.medicinalis* EU164975       SLNCPHR-LPNNKQCRCINARTAKDNRNPTCWA 75
(SEQ ID NO38)
*L.rubellus* DR008243       S-PCPG--LQNNKQCYCF-------------- 57 (SEQ ID NO 15)
Neuromacin EU156754       SK<u>H</u>CPGV-LKNNKQC<u>H</u>CY-------------- 59 (SEQ ID
NO 28)
*B.glabrata* CK989857       S-TCPLS--SEAFQCQCYT-------------- 62 (SEQ ID NO 16)
*A.californica* DQ489547       S-TCPFTRTDKAYQCQCKK------------- 76 (SEQ ID NO
10)
                                    \* \*\*    \*\*\* \*

B

Lumbricin-1 AF060552
MSLCISDYLYLTLTFSKYERQKDKRPYSERKNQYTGPQFLYPPERIPPQKVIKWN
EEGLP 60
PP-1     AY167144 -------------
MYSKYERQKDKRPYSERKDQYTGPQFLYPPDRIPPSKAIKWNEEGLP 47
***Hm*-lumbricin** EU156756 ------------
MFSKYERQKDKRSYGERFSMFTGPQFISPPERIKPNKILQWDGEGMP 47
                              \*\*\*\*\*\*\*\*\*\* \* \*\*  \*\*\*\*\* \*\* \*\* \* \*  \* \*\* \*

Lumbricin1   AF060552       IYEIPGEGG---HAEPAAA- 76 (SEQ ID NO 12)
PP-1         AY167144       MYEVLPDGAGAKTAVEAAAE 67 (SEQ ID NO 14)
***Hm*-lumbricin** EU156756       IYATS---------GAAAE 57 (SEQ ID NO 4)
                           \*        \*\*\*

Figure 5
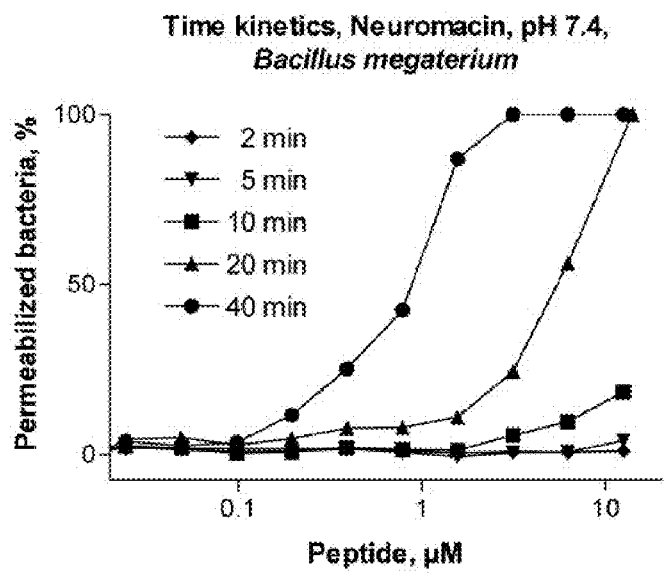
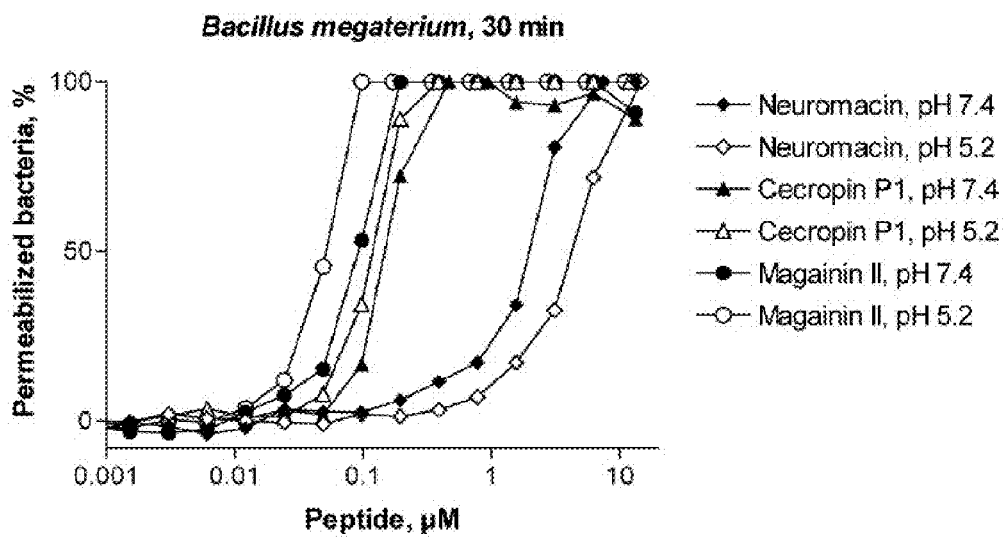

Figure 7
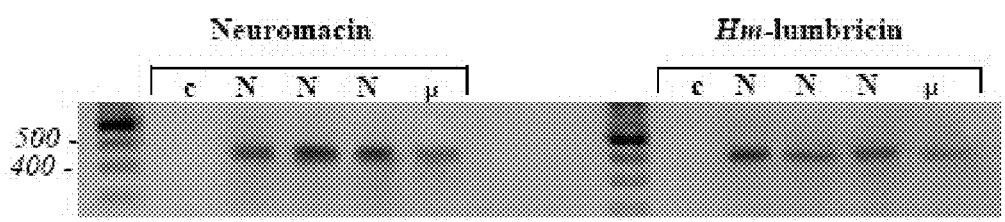
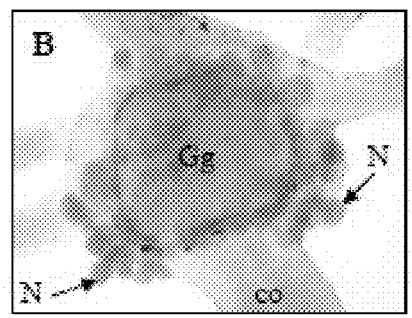
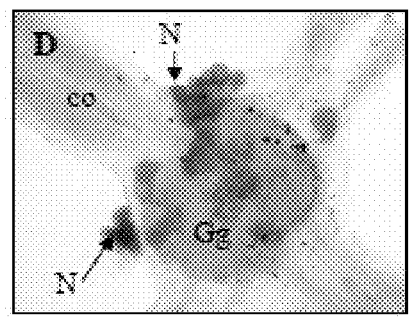
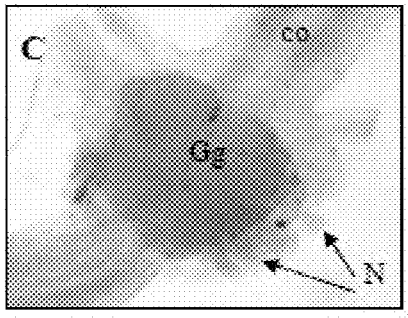
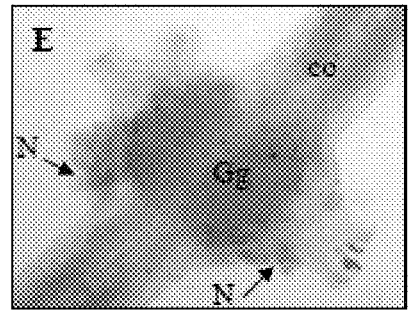

Figure 8
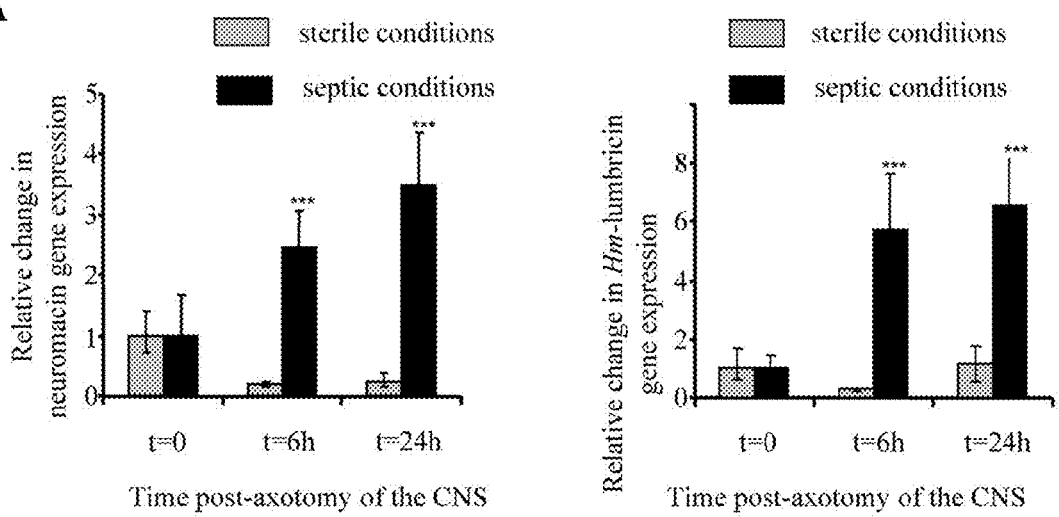
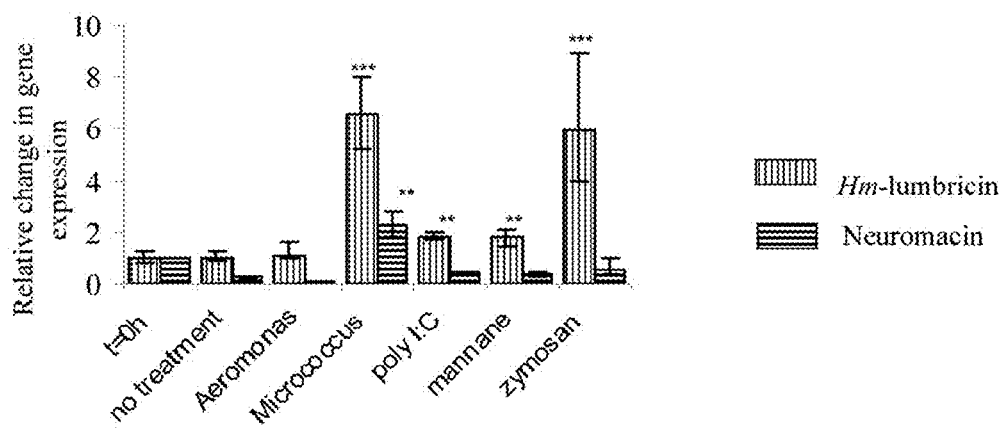

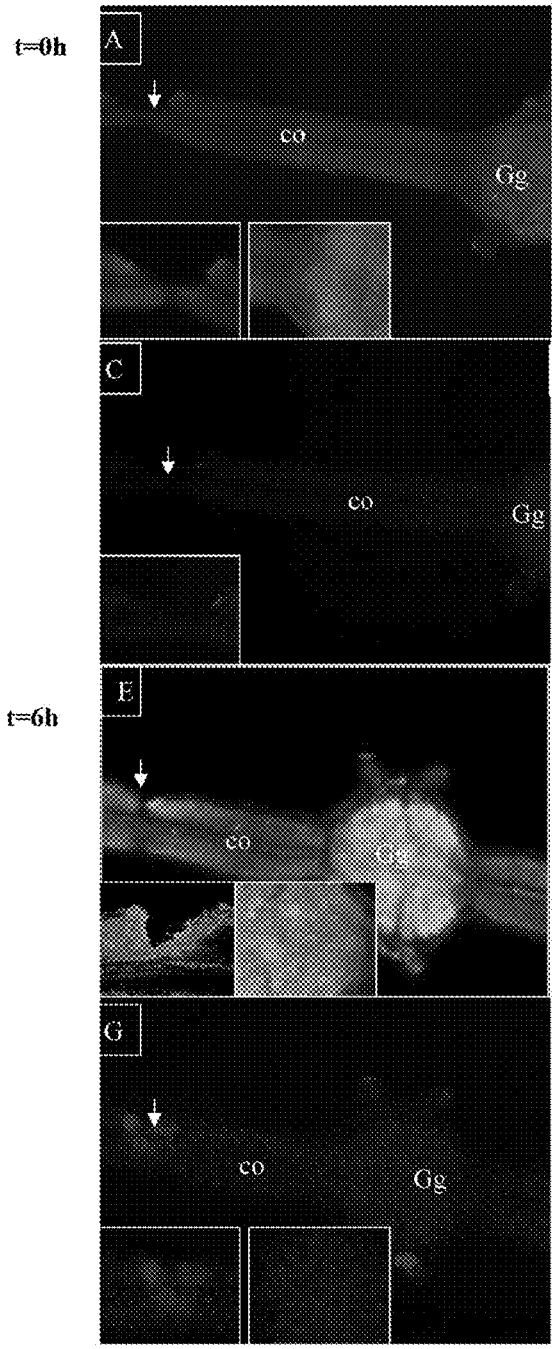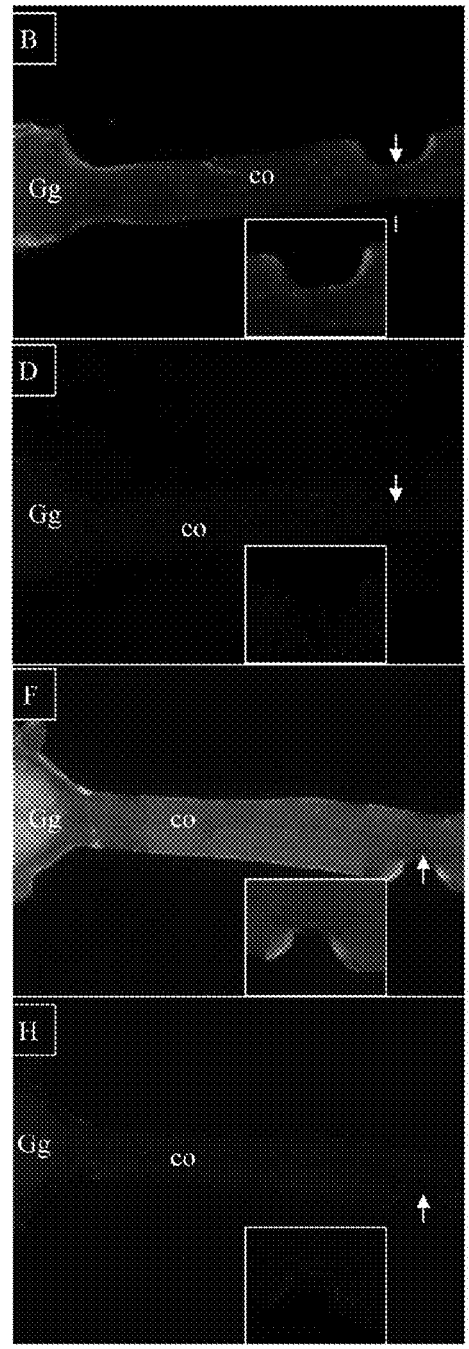
Figure 9

PEPTIDES HAVING ANTIMICROBIAL AND NEUROTROPHIC ACTIVITY AND USES THEREOF

The present invention relates to a method for treating neurodegenerative diseases, peptides having both antibacterial and neurotrophic activity and pharmaceutical compositions containing the same.

The population in the industrialised countries is rapidly ageing due to a greater life expectancy, and an ever-increasing number of people are afflicted with neurodegenerative diseases making a global issue out of these diseases.

Neurodegenerative diseases result from the gradual and progressive loss of neural cells, to leading to nervous system dysfunction, and may have next to ageing various causes (e.g. environmental influences, genetic defects). Till now more than 600 neurological disorders are known.

The major known risk factors for neurodegenerative disease include certain genetic polymorphisms and increasing age. Other possible causes may include gender, poor education, endocrine conditions, oxidative stress, inflammation, stroke, hypertension, diabetes, smoking, head trauma, depression, infection, tumors, vitamin deficiencies, immune and metabolic conditions, and chemical exposure. Because the pathogenesis of many of these diseases remains unknown, also the role of environmental factors in these diseases may be considered.

In order to treat neurodegenerative diseases several medicaments comprising one or more active compounds like Piracetam, Nimotop, Vinpocetin, Gliatilin, Cerebrolysin, Cytoflavin etc. are regularly employed. The compounds known in the art have varying modes of action. Cerebrolysin, for instance, a peptide based drug produced from purified animal brain proteins by standardized enzymatic breakdown, is exerting nerve growth factor like activity on neurons from dorsal root ganglia, neurotrophic and neuroprotective effects. Although these drugs are efficient there is still a need for new and efficient compounds.

Because of its multiple vital functions, it is critical that the central nervous system (CNS) be successfully defended against pathogens. Until recently, this organ was considered to be immunologically inert and isolated from the peripheral immune system. However, it is now well established that immune surveillance and inflammatory responses do occur within this compartment. Indeed, in response to either cerebral injury or systemic bacterial infection, the CNS launches a well organized immunological reaction that encompasses both neural components and peripheral immune system cells. Within the mammalian CNS, resident glial cells, including astrocytes and microglia, have been shown to initiate a characteristic innate immune response by producing and releasing antimicrobial peptides, cytokines and chemokines. These circulating molecules promote the destruction of the invading bacteria, the permeabilization of the blood brain barrier (BBB), and the recruitment of peripheral leukocytes to the CNS and the activation of their effector functions, including further production of cytokines as well as phagocytosis by peripheral macrophages. The specific outcome of this neuroinflammatory response, which has both beneficial and detrimental aspects, depends on the context of the insult and on the duration of the inflammation. On the positive side, increased immune activity rapidly initiates the killing of bacteria and the removal of apoptotic cells and cellular debris, while also playing an important role in to neuroprotection and repair by inducing the production of neurotrophic factors. In fact, several recent observations suggest that induction of regeneration of normal CNS function may depend critically upon the co-initiation of an immune response. On the negative side, excessive and/or chronic glial reactivity, in conjunction with the presence of adaptive immune cells within the CNS, can damage the CNS by inducing neuronal death and by blocking axonal myelination. An important question that remains unanswered is how the vertebrate immune system can be both friend and foe to the damaged tissue. Some of the difficulty in obtaining an answer probably lies in the conflation of the innate and adaptive immune responses, which makes the vertebrate immune response quite complex and difficult to dissect.

In this context, the inventors have made a detailed study of the immune response that can be evoked in the injured CNS of an invertebrate, namely the medicinal leech (Hirudo medicinalis), in which the immune response appears to lack a deleterious component. Invertebrates, being devoid of adaptive immunity, are excellent model systems for exploring the molecular basis of innate immunity. For example, the initial evidence for the pivotal role of the Toll receptor family in immunity was discovered in *Drosophila*, and only later in mammals. Another example is the discovery of the first antimicrobial peptides by Hans Boman in the insect *Hyalophora cecropia*. Antimicrobial peptides are now considered as important effectors of the innate immune systems of both invertebrates and vertebrates. Most reports on immune effectors in invertebrates have tended to focus on their involvement in the systemic antiinfectious response. However, some studies have described the presence of immune molecules in the nervous systems of insects and nematodes, both members of the ecdysozoan group. Indeed, several Toll-like receptors (TLR) and some molecules of the TLR signalling pathway have been detected in glial and neuronal cells of *Drosophila*, and appear to have a role in neural development in the larvae. In *Caenorhabditis elegans*, an ortholog of the *Drosophila* toll gene was shown to be expressed in pharyngeal neurons, where it participates in defensive behaviour by discouraging the worm from ingesting pathogenic bacteria. In the medicinal leech, a member of the lophotrochozoan group reported that several central neurons express HmCRIP, an ortholog of the mammalian Cysteine Rich Intestinal Protein (CRIP) that is known to regulate the inflammatory response through control of Th1/Th2 differentiation in rodents.

Several features make the CNS of the medicinal leech particularly attractive as a model system for the exploration of interactions between the nervous and immune systems. These features include simplicity, a fixed number of neurons, and consistency from animal to to animal, which allow the recognition, characterization and repeated study of identified neurons, at all developmental stages and following specific perturbations, such as mechanical or septic trauma. The leech CNS is comprised of a fixed number of midbody segmental ganglia linked to each other by longitudinal nerves known as connectives. Most segmental ganglia have a complement of ~400 neurons and 8 giant glial cells, along with a large population of microglial cells.

In the context of the observations the inventors have surprisingly discovered that a bacterial challenge promotes the capacity of the medicinal leech CNS to regenerate and restore normal function in response to injury. If the nerve cord of this annelid is crushed or partially cut, axons grow across the lesion and conduction of signals through the damaged region is restored within a few days, even when the nerve cord is removed from the animal and maintained in culture. By contrast, when the mammalian spinal cord is injured, regeneration of normal connections generally fails. In the leech, the process of regeneration begins with a rapid activation of microglial cells leading to their accumulation at the lesion site. Like their counterparts in the mammalian brain, leech microglial cells are involved in phagocytosis of damaged tissue.

The leech nerve cord consists of a chain of interconnected segmental ganglia that resides within the ventral blood sinus. It is encapsulated by a tough fibrous sheath that may, like the mammalian blood-brain barrier, limit the exchange of macromolecules and cells with the blood which continuously bathes it. The virtually intact CNS (except for the cut lateral nerves) can be easily removed from the animal and maintained in culture for weeks in the absence of peripheral immune system components and blood cells that might infiltrate the CNS after injury. Consequently, studies can be focused exclusively on the immune response of the CNS itself.

Thus one aim of the invention is to provide new treatment of neurodegenerative diseases based on the discovery by the inventors of novel antibacterial peptides, isolated from the medicinal leech nervous system and have been shown to enhance the capacity of the leech CNS to regenerate.

Thus the invention relates to a method for preventing a break out of a neurodegenerative disease in an individual and for treating an individual suffering from a neurodegenerative disease comprising the administration of an effective amount of:

either at least one peptide comprising or consisting of the amino acid sequence SEQ ID No 28 or at least one peptide having any sequence derived from said SEQ ID NO: 28, with the proviso that said peptides have a neurotrophic activity, or at least one peptide comprising or consisting of the amino acid sequence SEQ ID No 4 or at least one peptide having any sequence derived from said SEQ ID NO: 4, with the proviso that said peptides have a neurotrophic activity.

In a preferred embodiment of the invention, the peptides derived from the peptide of SEQ ID NO: 28 share the same cystein pattern and comprise at least 7 cysteine residues; in a best mode, said peptides conserve the following arrangement of the 8 cysteine residues in their amino sequence and comprise one sequence selected from the group comprising:

SEQ ID NO 30: $CX_6CX_{14}CX_3CX_9CX_6CX_8CXC$,

SEQ ID NO 31: $CX_6CX_{14}CX_3CX_9CX_6CX_9CXC$,

SEQ ID NO 32: $CX_6CX_{14}CX_3CX_9CX_6CX_{10}CXC$,

SEQ ID NO 33: $CX_6CX_{14}CX_3CX_9CX_7CX_8CXC$,

SEQ ID NO 34: $CX_6CX_{14}CX_3CX_9CX_7CX_9CXC$,

SEQ ID NO 35: $CX_6CX_{14}CX_3CX_9CX_6CX_{10}CXC$, wherein C is a cysteine residue, X any amino acids and where the number corresponds to the number of amino acids between each cysteine residue.

In another preferred embodiment of the method according to the invention, said peptides derive from the peptides of SEQ ID NO: 4 or 28 by substitution, and/or suppression, and/or addition of one or several amino acids, of the above-mentioned peptides, and/or by modification of at least one —CO—NH— peptide linkage of the peptide chain of the above-mentioned peptides, particularly by introduction of a retro or retro-inverso type linkage, and/or by substitution of at least one amino acid of the peptide chain of the sequence or of the above-mentioned peptide, with a non-proteinogenic amino acid, or said peptides correspond to fragment of SEQ ID NO: 4, in particular, peptides or fragments of peptides having more than 50%, preferably more than 55%, preferably more than 60% and more preferably more than 65% of homology, provided that the neurotrophic activity is maintained.

In a further advantageous embodiment of the method according to the invention, the at least one peptide is selected from the group comprising SEQ ID NOS 2, 4, 6, 8, 10, 12, 14, 15, 16, and 28.

By the expression "peptide" it is meant peptides that have been isolated and/or peptides whose sequence has been deduced from in silico analysis of EST/genome databanks from living organisms, for example from invertebrates like *Theromyzon tessulatum, Lumbricus rubellus Aplysia californica, Biomphalaria glabrata, Pheretima tschiliensis, Hydra magnipapillata* and *Hirudo medicinalis*, but it also covers synthetic peptides having the sequence of said isolated peptides. Synthetic peptides can be prepared by chemical (peptides synthesis) or biological ways well known from a man skilled in the art (recombinant production).

Thus, peptides having the SEQ ID NOS: 4, 12 and 14 can have an amino acid sequence wherein one or more amino acids are substituted or suppressed everywhere inside said sequence or wherein one or more proteinogenic amino acids, i.e. natural amino acids, are added to said sequence, provided that, in each of above cases the neurotrophic activity of the peptides would be conserved.

Peptides having the SEQ ID NO: 4, 12 and 14 can also have an amide linkage (—CO—NH— peptide linkage) modified by introduction of a retro amide linkage (—NH—CO— peptide linkage) or a retro inverso amide linkage (—NH—CO— peptide linkage and an inverse absolute configuration of the amino acid) provided that, in each of above cases the neurotrophic activity of the peptides would be conserved.

By the expression "non-proteinogenic amino acids", it must be understood either amino acids not found in proteins (like carnitine, GABA, or L-DOPA), or not coded for in the standard genetic code (like hydroxyproline and selenomethionine) provided that, in each of above cases the neurotrophic activity of the peptides is conserved.

According to the invention, the neurodegenerative disease is selected from Alzheimer's disease, Parkinson's disease, amyotrophic lateral sclerosis (ALS), peripheral neuropathies, neural injury secondary to hypoxia, ischemia or trauma, processes involving apoptosis, or Huntington's disease.

In the method according to the invention, the peptide may be provided under any dosage form or pharmaceutical composition usable for intravenous, intramuscular, spinal, epidural, transdermal, subcutaneous, parenteral, oral, enteral or rectal administration. All these forms and compositions are well known from the one skilled in the art.

According to a preferred embodiment of the present invention the pharmaceutical composition may further comprise at least one additional pharmaceutically active component, which may exhibit similar properties when administered to an individual or which may cause other reactions in the treated patient In a preferred embodiment the peptides further have an antibacterial activity.

According to a preferred embodiment of the present invention in the method according to the invention the pharmaceutical composition may comprise the peptides in an amount between 0.1 g/g to 100 mg/g, preferably 1 g/g to 80 mg/g.

The invention also concerns purified peptides having antimicrobial and neurotrophic activity selected form SEQ ID NOS 4 and 28 and pharmaceutical composition comprising at least one peptide selected from SEQ ID NOS 4 and 28 and optionally a pharmaceutical acceptable excipient and/or carrier.

These two peptides are issued from *Hirudo medicinalis*, SEQ ID NO 28 is named Neuromacin and SEQ ID NO 4 is named Hm-lumbricin.

Neuromacin and analogous peptides of SEQ ID NOS 6, 8, 15, 16 and 10 share the same cysteine pattern (7 to 8 cysteines).

SEQ ID NO 2 comprises SEQ ID NO 28 and a signal peptide which is cleaved off said peptide leading thus to the active peptide.

The invention also concerns a nucleotide sequence coding for a polypeptide of SEQ ID NOS 2 or 4, said nucleotides having respectively the sequences SEQ ID NO 1 and SEQ ID NO 3.

The invention also concerns a recombinant vector, especially a plasmid, a cosmid, a phage or a DNA virus, containing a nucleotide sequence as defined above. Said recombinant vector may contain all the elements necessary for the expression in a host cell of the polypeptides coded by the nucleic acids defined above, inserted in said vector.

The invention also concerns a host cell, in particular chosen from bacteria, viruses, yeasts, fungi, plants or mammalian cells, the said host cell being transformed, especially by means of a vector as defined above in such a way that its genome contains a nucleotide sequence as previously defined.

An object of the present invention concerns a pharmaceutical composition comprising at least one peptide of SEQ ID no 4 or 28 and optionally a pharmaceutical acceptable excipient and/or carrier.

The invention also concerns a method of treating a bacterial infection in an animal or human, said method comprising administering a therapeutically effective amount of the substance or composition to the animal or human, said substance or composition comprising a peptide selected from SEQ ID NOS 4 or 28.

The invention also concerns either at least one peptide comprising or consisting of the amino acid sequence SEQ ID No 28 or at least one peptide having any sequence derived from said SEQ ID NO: 28, with the proviso that said peptides have a neurotrophic activity, or at least one peptide comprising or consisting of the amino acid sequence SEQ ID No 4 or at least one peptide having any sequence derived from said SEQ ID NO: 4, with the proviso that said peptides have a neurotrophic activity, for their use for preventing a break out of a neurodegenerative disease in an individual and for treating an individual suffering from a neurodegenerative disease.

The present invention is further illustrated by the following figures and examples, however, without being restricted thereto.

FIG. 1 illustrates the effects on nerve regeneration of exposure of excised leech CNS to live or heat-killed bacteria (A) Diagram of the leech CNS in culture preparation. Neuron cell bodies (N) within ganglia (Gg) project axons into connectives (co) towards adjacent ganglia. V indicates the location of the cut of one of the two connectives linking two segmental ganglia. Microglial cells, evenly distributed in the nerve cord, are represented by dots. The nervous system is protected by a fibrous capsule (Ca). (B-D) Sequential micrographs, taken 24 hr apart, from one (J1) to eight days (J8) post-axotomy, documenting the regeneration of the severed connective nerve. (B) Preparation in sterile culture medium, (C) incubated with live bacteria, and (D) incubated with killed bacteria.

FIG. 2 illustrates RP-HPLC of acidic extract obtained from leech nerve cords challenged with bacteria. After prepurification by solid phase extraction, the 60% ACN eluted material was loaded onto a C18 column (250×4 mm, Vydac). Elution was performed with a linear gradient of acetonitrile in acidified water (dotted line), and absorbance was monitored at 225 nm. Each individually collected peak was tested for its antimicrobial activity by solid plate assays. Two fractions containing neuromacin and Hm-lumbricin were found to be active. These fractions were further purified by two additional RP-HPLC purification steps and exact mass of purified peptides was determined by MALDI TOF-MS (left inset). Second RP-HPLC step of Hm-lumbricin (right inset). Analysis of neuromacin by MALDI TOF-MS shows a m/z value of 6,709.74 MH+.

FIG. 3 illustrates Neuromacin (A) and Hm-lumbricin (B) cDNAs. Deduced amino acid sequences of the ORF are shown under the nucleotide sequences. Signal peptide is in italics. Initiation and stop codons are framed. Polyadenylation signals are underlined.

FIG. 4 SHOWS sequence comparisons of neuromacin and Hm-lumbricin. (A) Neuromacin (EU156754) was compared to theromacin, an antimicrobial peptide firstly characterized from the leech *Theromyzon tessulatum* (AY434032) and later from the medicinal leech (EU164975), the earthworm *Lumbricus rubellus* (DR008243) and the molluscs *Aplysia californica* (DQ489547) and *Biomphalaria glabrata* (CK989857). (B) Hm-lumbricin (EU156756) was compared to lumbricin-1, an antimicrobial peptide initially characterized from the earthworm *Lumbricus rubellus* (AF060552) and the Asian worm *Pheretima tschiliensis* (AY167144).

FIG. 5 illustrates membrane permeabilization of *B. megaterium* induced by neuromacin. Membrane damage of the bacteria was measured fluorometrically using the dye SYTOX Green. The binding of the dye to the DNA in membrane-compromised target cells resulted in an increase of fluorescence. Antibacterial activity of the peptides is expressed as a percentage of permeabilized bacteria. (A) Time kinetics of membrane permeabilization induced by neuromacin measured for different doses at various incubation periods. (B) Membrane permeabilizing effects of neuromacin (rhombs) in comparison with cecropin P1 (triangles) and magainin II (circles) after 30 min of incubation of *B. megaterium* with each peptide at various concentrations, at pH 5.2 (open symbols) and at pH 7.4 (closed symbols).

Figure 6:
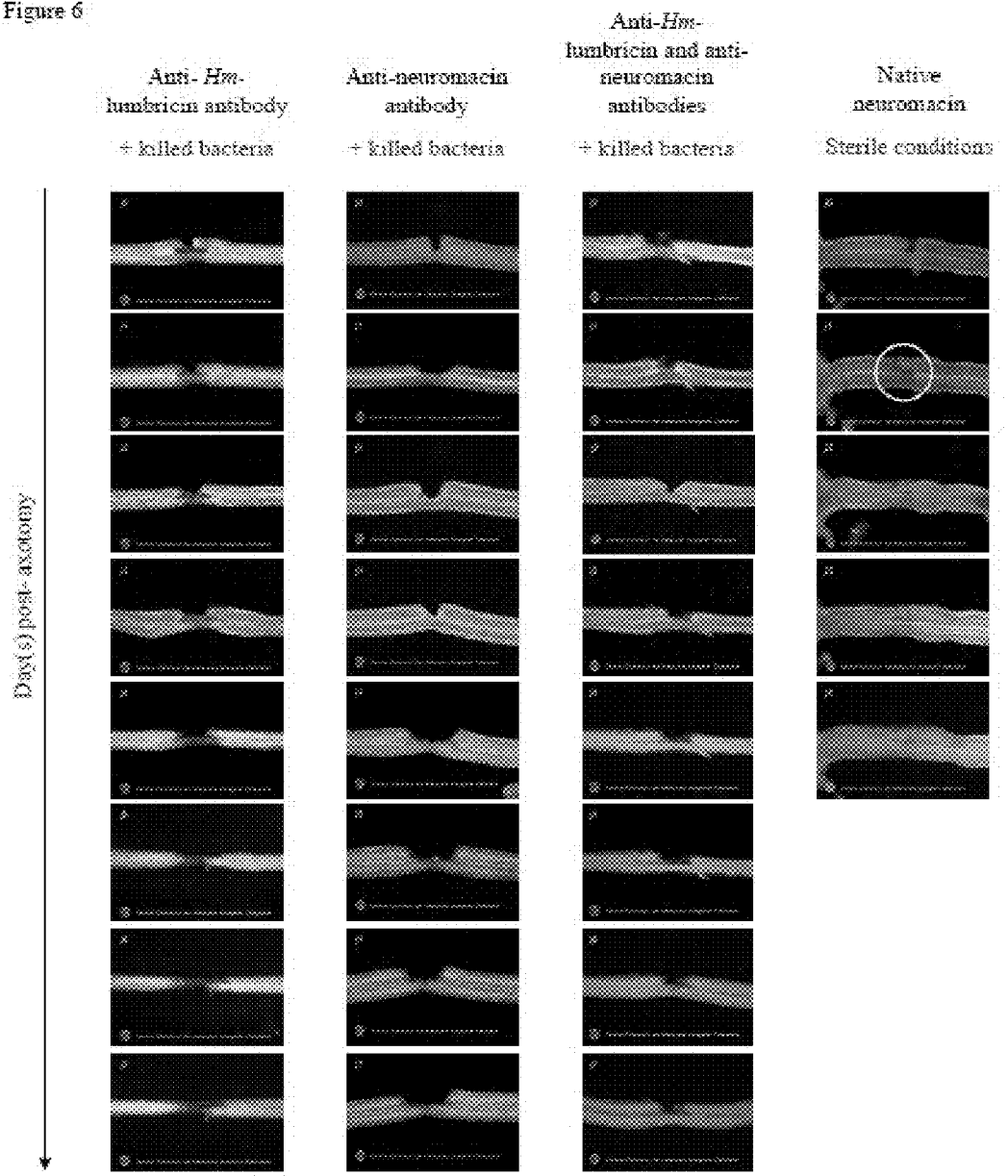

FIG. 6 illustrates the sectioning of one side of the paired connective nerve linking adjacent segmental ganglia was performed on excised nerve cords maintained in culture. Different substances were added to the culture medium and their regenerative impact on leech damaged nerve cord was evaluated by monitoring the progress of nerve repair in the presence or absence of bacteria. Sequential micrographs were taken 24 hours apart, from one (J1) to eight days (J8) post-axotomy, documenting the regeneration of the severed connective nerve.

FIG. 7 illustrates the analysis of neuromacin and Hm-lumbricin gene expression sites in isolated cells and in bacteria challenged nerve cords. (A) Neuromacin and Hm-lumbricin transcripts were amplified by RT-PCR from single neurons "N" and from single microglial cells "µ" isolated from challenged nerve cords. The amplifications were performed with an oligodT as reverse primer to avoid any amplification of the genomic DNA. ISH with digoxygenin dUTP labeled neuromacin (B) and Hm-lumbricin antisense riboprobes (D) from glia deficient nerve cords incubated for 6 hours with bacteria. Nerve cords depleted of microglial cells were obtained by opening the capsule surrounding the ganglia, which makes the neurons visible. Transcripts were detected in the cell bodies of neurons "N" confirming the data obtained by single cell PCR. No signals were detected with the neuromacin (C) and Hm-lumbricin (E) sense riboprobes. Co: connective; Gg: ganglia FIG. 8 illustrates the quantification of the levels of expression of neuromacin and Hm-lumbricin in leech nerve cords by real time PCR analysis using the ΔΔCt method. Analysis of RNA levels in an axotomized CNS was assessed 0, 6 h, and 24 h, after addition of a mix of heat killed *A. hydrophila* and *M. nishinomiyaensis* to the medium. (A) and 0 h and 6 h in presence of various microbial components (B). A plot of the log cDNA dilution versus ΔCt was generated for each target gene tested to validate the qPCR experiments. Treatment of triplicate data. Reference (18S) and targets were amplified in separate wells (n>10 in all cases). *, $P<0.001$; , $P<0.01$; for each conditions, the difference between the controls (t=0 h) and the challenged nerve cords (t=6 h) is highly significant (T-test).

FIG. 9 illustrates the appearance of neuromacin and Hm-lumbricin in the microglial cells of injured CNS incubated for 6 hours with killed bacteria. Double staining was performed on injured nerve cords at t=0 and t=6 h post-axotomy, by using the fluorescent nuclear dye Hoechst 33258 (C, D, G, H) and either the anti-neuromacin (A, E) or the anti-Hm-lumbricin (B, F) polyclonal antibody Immunodetection was performed using FITC-labeled secondary antibody. Results show an accumulation of neuromacin (E, inset) and Hm-lumbricin (F, inset) at the lesion site 6 hours post-axotomy in correlation with an accumulation of microglial cells as revealed by nuclear staining (G, H). Neuromacin but not Hm-lumbricin was also immunodetected within the microglial cells covering the ganglia and the connectives (E, inset). At this magnification, microglial cells appear as small dots. Lesion site: Gg: ganglia, co: connective.

Figure 10:
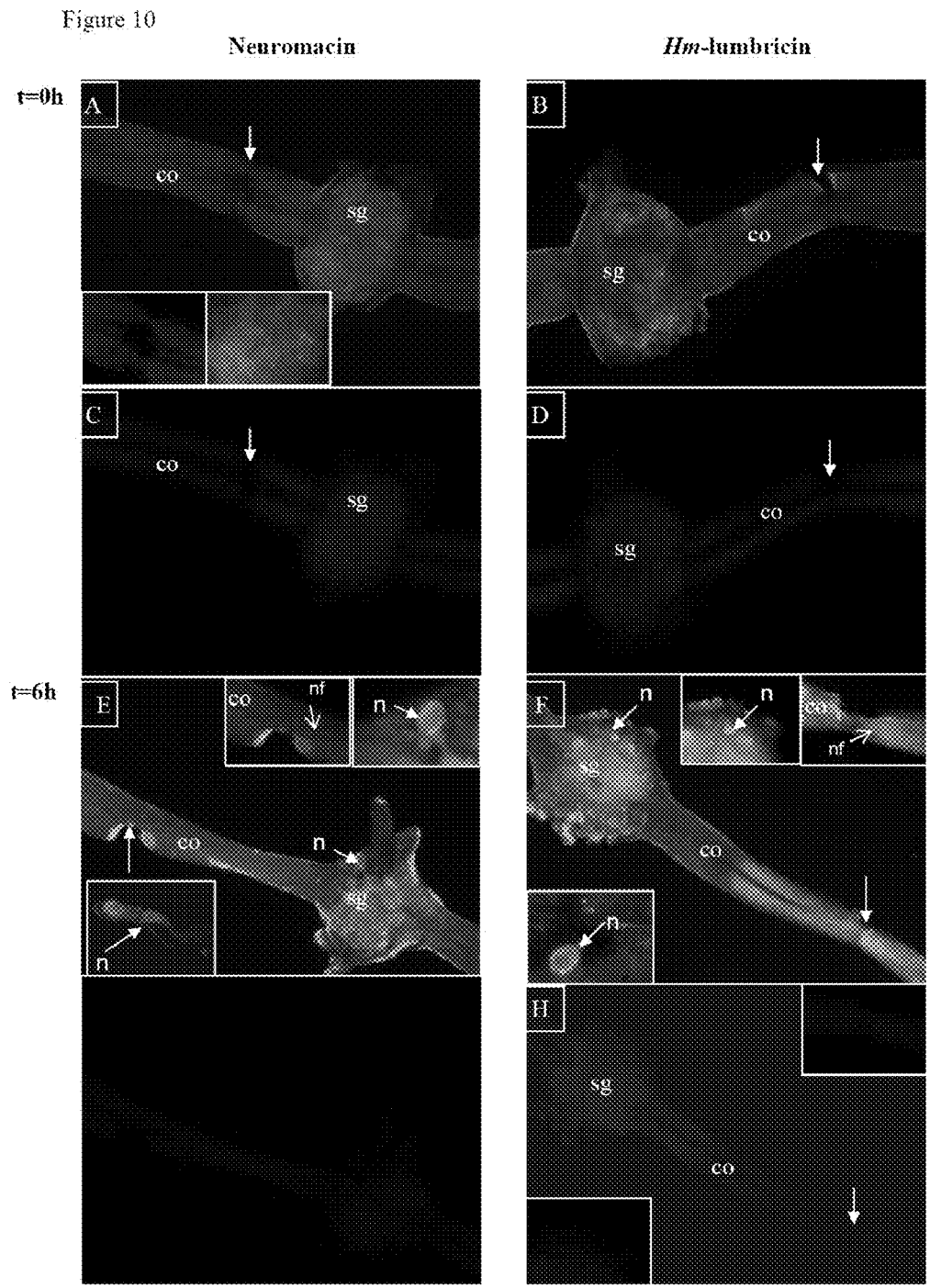

FIG. 10 illustrates the appearance of neuromacin and Hm-lumbricin in neurons and in nerve fibers of the injured connectives of CNS incubated for 6 hours with killed bacteria. Double staining was performed on glia deficient nerve cords at t=0 and t=6 h post-axotomy, by using the fluorescent nuclear dye Hoechst 33258 (C, D) and either the anti-neuromacin (A, E) or the anti-Hm-lumbricin (B, F) polyclonal antibody Immunodetection was performed using FITC-labeled secondary antibody. Results show an accumulation 6 hours post-axotomy of neuromacin (E) and Hm-lumbricin (F) at the lesion site (arrows) where no microglial cells accumulate as shown by the absence of nuclear staining. (G, H). In these preparations, neuromacin and Hm-lumbricin were immunodetected in neurons (n) and in nerve fibers (nf) of the injured connectives (E, F, top insets). Confocal laser micrographs show an intense Hm-lumbricin and neuromacin immunoreactivity in neurons isolated from challenged nerve cords (E, F, bottom insets). Lesion site: Gg: ganglia, co: connective.

Figure 11:
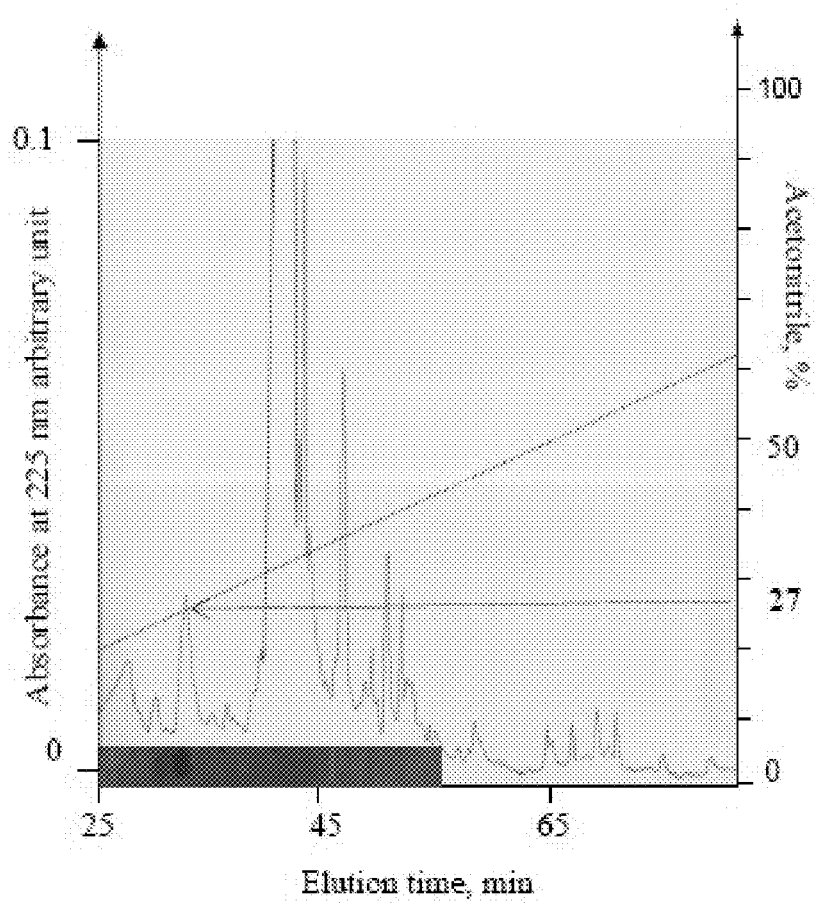

FIG. 11 illustrates RP-HPLC of acidic extract obtained from the culture medium of nerve cords challenged with zymosan. After prepurification by solid phase extraction, the 60% ACN eluted material was loaded onto a C18 column (250×2.1 mm, 218TP52 Vydac). Elution was performed with a linear gradient of acetonitrile in acidified water (dotted line), and absorbance was monitored at 225 nm. Each individually collected peak was tested by DIA. One fraction eluted at the same percentage of ACN (27%) than the purified Hm-lumbricin (see FIG. 2) was recognized by the anti-Hm-lumbricin antibody, evidencing the presence of Hm-lumbricin in the extracellular medium.

MATERIALS AND METHODS

Collection and treatment of the nerve cords: Adult leeches, *Hirudo medicinalis* species, weighting 2-3 g were purchased from a commercial supplier (Ricarampex, France). Animals were kept in artificial pond water and starved up to 3 weeks before use. Leeches were anaesthetised in 10% ethanol-spring water for 20 min and the nerve cords were removed according to the protocol of Nicholls et al (*J Neurophysiol*, 1968, 31:740-756.). After three successive baths in antibiotics, cords were placed in Leibowitz-15 (L-15, Gibco) culture medium supplemented with 2% fetal calf serum, 0.6% glucose and gentamicin (10 mg/ml) (*Nature*, 1979, 281:67-69). Connectives between ganglia were injured in a standard manner using a pair of sterilized fine iridectomy scissors. Axotomized nerve cords were separately incubated in L-15 medium containing different microbial components: $3 \times 10^7$ CFU/ml of heat killed or live bacteria, 10 μg/ml of polyI:C (Invivogen), 100 μg/ml of zymosan (Invivogen,) and 100 μg/ml of mannane (Invivogen) for different time (t=0 to t=8 days) at room temperature. Incubations without microbial components or bacteria were performed in the same conditions as controls. All the steps were performed under sterile conditions.

Nerve cords depleted of microglial cells were obtained 6 hours after having opened the capsule surrounding the ganglia with fine scissors.

Microorganisms: The Gram-positive and Gram-negative bacteria *Micrococcus nishinomiyaensis* and *Aeromonas hydrophila* respectively were isolated from the natural environment of *Hirudo medicinalis*. These bacterial colonies, which are present in the water, were selected from agar plate under aerobic conditions at room temperature using a random isolation grid. The Gram-positive bacteria *Bacillus megaterium* was used for the SYTOX Green assay.

Time-lapse movies on axotomized nerve cords: Dissected nerve cords (three per conditions) were pinned in a dish coated with silicone rubber (Sylgard 184) containing supplemented L-15 medium under sterile conditions and one connective of each nerve cord was cut. To measure the effect of bacteria on the regeneration process, a mix of either live or heat-killed *A. hydrophila* and *M. nishinomiyaensis* ($3 \times 10^7$ CFU/ml) was added to the culture medium. Controls were performed in the absence of bacteria. To determine the effect of the antimicrobial peptides on the capacity of the leech nerve cord to regenerate, anti Hm-lumbricin and/or anti neuromacin antibody(ies) at a 1:100 dilution was(ere) added to the culture medium containing killed bacteria. Native neuromacin was also added to the medium at the final concentration of 4 μM in absence of bacteria.

Pictures were taken every 24 hours for 1 week (objective X5) using a LEICA inverted microscope DMIRE2. Images were taken using the Bioposition V3.0 software developed on the Matrox MIL7.5 Base Library by Gilles Courtand from the CCMIC (Centre Commun de Mesures Imagerie Cellulaire) of the University of Lille 1, France.

Antimicrobial assays: After each purification step, antibacterial activity was monitored by a solid plate assay as described in previous studies (14). The minimal inhibitory concentration (MIC) and the minimal bactericidal concentration (MBC) were determined according to the method of Hancock (http://cmdr.ubc.ca/bobh/showmethod.php?methodid=79). Permeabilization of bacterial membranes and pore-forming activity were assayed as previously described (Herbst, R et al. (2002), J Biol Chem 277:22353-22360; Leippe, M. et al. 1991. Proc Natl Acad Sci USA 88:7659-7663).

Purification and identification of the peptides: 100 nerve cords challenged for 6 hours with a mix of killed bacteria were homogenized in phosphate buffered saline pH 7.5. Liquid was immediately centrifuged at 10,000 g at 4° C. for 20 min and the supernatant was acidified by adjusting the pH to 3.9 with 1 M HCl. Centrifugation (10,000 g at 4° C. for 20 min) was then used to clarify the supernatants, which were loaded onto Sep-Pak C18 Vac cartridges (Waters). Elution steps were performed with 2% and 60% acetonitril (ACN) in 0.01% trifluoroacetic acid water. The pre-purified fractions were then lyophilized, reconstituted in pure water and tested for antimicrobial activity as described below. Only the 60% ACN eluted fractions were active and submitted to purification by reversed-phase high pressure liquid chromatography (RP-HPLC). All the purification steps were carried out on a Beckman™ Gold HPLC system.

Step 1: Aliquots of the 60% Sep-Pak fractions were subjected to RP-HPLC on a Sephasyl C18 column (250×4.1 mm, 218TP54 Vydac™). Elution was performed with a linear gradient of 2-62% ACN in acidified water over 90 min at a flow rate of 1 ml/min Fractions corresponding to absorbance peaks were collected in polypropylene tubes, lyophilized, reconstituted in water and tested for antimicrobial activity.

Step 2: Active fractions were further loaded onto a C18 column (250×2.1 mm, 218TP52 Vydac™) with a gradient consisting in 2-25% ACN in acidified water for 10 min and 25-35% ACN for 40 min at a flow rate of 0.2 ml/min Fractions were collected and treated as above.

Step 3: One additional step was performed on a narrow bore C18 reversed phase column (150×2 mm, Waters) at a flow rate of 0.2 ml/min using the ACN gradient described in the step 2. The purity assessment and the molecular mass determination of the peptides were carried out by matrix-assisted laser desorption/ionisation-time of flight (MALDI-TOF) instrument (DE STR PRO, Applied Biosystem). N terminal sequencing of the purified peptides was performed by automated Edman degradation on a pulse liquid automatic peptide sequenator (Beckman).

Hm-lumbricin exocytosis: The culture medium of 20 nerve cords challenged with zymosan (see collection and treatment of the nerve cords) was acidified and prepurified as described above. The entire 60% Sep Pak fraction was loaded onto a C18 column (250×2.1 mm, 218TP52 Vydac™) with a gradient consisting in 2-62% ACN in acidified water for 90 min Fractions were collected, lyophilized, reconstituted in 10 µl of pure water and tested by Dot Immunobinding Assay (DIA) according to Salzet et al. (*Eur J Biochem*, 1994, 221:269-275). Briefly, one of the 10 µl samples was spotted onto a nitrocellulose membrane and was incubated with the Hm-lumbricin antiserum (1/1000). Bound antibodies were detected with a goat antirabbit IgG conjugated to horseradish peroxidase by using a chemoluminescence kit (ECL; Amersham).

cDNA cloning: Complete cDNA for Hm-lumbricin was obtained from an expressed sequence tag (EST) library created from the nervous system of *Hirudo medicinalis* (http://www.cns.fr/externe/English/Projets/Projet_PE/PE.html). Hm-lumbricin cDNA was amplified from the cDNA prepared for neuromacin by polymerase chain reaction (PCR) using the sense oligonucleotide 5'-ATGGAGGAGGAAATTGAA-GAACTCC-3' (SEQ ID NO: 17) and the antisense oligodT primer.

cDNA for neuromacin was cloned using two steps PCR amplification:

Step 1: Reverse-transcriptase PCR (RT-PCR): Total RNA from leech nervous system was extracted using Trizol (Life Technologies). RNA (3 µg) was transcribed into single stranded cDNA using oligo(dT)18-adaptator primer, 5'-CGAGTCGACATCGATCG(T)18-3' (SEQ ID NO: 18) (Kit superscript Tm, GIBCO/BRL, protocol of the manufacturer). One fourth of the reaction was amplified by PCR using the oligodT primer and degenerate sense oligonucleotide pool whose sequence is deduced from Asp1-Trp6 with a designed 5' flanking sequence 5'-GA(C/T)TG(C/T)TA(C/T)GA(A/G)GA(C/T)TGG-3' (SEQ ID NO: 19). PCR was performed for 25 cycles using one unit of Taq polymerase (Appligene quantum) in 1.5 mM of MgCl2. The cycling parameters were: 94° C. for 1 min., 50° C. for 1 min. and 72° C. for 1 min.

Step 2: Rapid Amplification of 5'cDNA End. Reverse-transcription was performed using antisense oligonucleotides 5'-cagtcaggaatgacgttccaggcg-3' (SEQ ID NO: 20) deduced from the neuromacin cDNA sequence previously obtained. After first strand cDNA synthesis and addition of a poly-d(C) tail at its 3' end using a terminal transferase (GIBCO, protocol of the manufacturer), PCR was performed with an oligodG anchor primer and internal antisense primers deduced from the cDNA obtained in step 1: 5'-tcccctgtgaccgagttc-3' (SEQ ID NO: 21). PCR parameters were identical to those described in step 1.

All PCR products were ligated into the PGEMT easy vector (according to the protocol provided by the manufacturer) and transformed into competent *Escherichia coli* JM 109 cells (Promega).

Plasmids DNA were sequenced with a FM13/RM13 sequencing kit (Pharmacia Biotech) according to the manufacturer's instructions.

Gene Expression Analysis

RNA isolation and real time PCR analysis: Twenty leeches were used per conditions. Nerve cords incubated in the presence or absence of killed bacteria, poly I:C, mannane or zymosan (see above for details) were crushed, in 2 ml tubes prefilled with Qiazol reagent (Qiagen, France) and 1.4 mm ceramic beads, by shaking the mixture twice for 45 s at 6500 rpm in a Precellys®24 homogenizer (Bertin distributed by Ozyme, France). RNA extraction was performed according to the manufacturer and extracted total RNA was treated with RQ1DnaseI (Promega, France) to prevent contaminations with genomic DNA. First strand cDNA was generated from 2 µg of total RNA using random primers (Promega, France) and Superscript III reverse transcriptase (RT) kit (Invitrogen, France) in a final volume of 60 µl. Omitting RT or RNA from the reaction mixture resulted in non amplification control and non template control respectively. cDNA were treated with RNaseH (Promega, France) to optimize the amplification.

Real time PCR were performed with the Quantitect SYBRgreen PCR kit (Qiagen, France) by combining 1 µl of cDNA, 0.8 µM of each primer and 1× of SYBRgreen reagent in a final volume of 25 µl. The primers were designed with the Primer3 Input software (http://frodo.wi.mit.edu/cgi-bin/primer3/primer3_www.cgi) according to the conditions described in the PCR kit.

Hm-lumbricin:

(SEQ ID NO: 22)
5'-CCAATCGGCTCTCCTTACTC-3',

-continued (SEQ ID NO: 23)
5'-ACAGGCCCTCAGTTCATTTC-3';

Neuromacin:
(SEQ ID NO: 24)
5'-GTGGACGCCTGGAACGTCAT-3', (SEQ ID NO: 25)
5'-CTTGAGGACTCCAGGGCAGT-3'

18S:
(SEQ ID NO: 26)
5'-tgcggttatttcgattgtca-3', (SEQ ID NO: 27)
5'-agacaaatcgctccaccaac-3'

Real time PCR was conducted on an Applied Biosystem 5700 using hot start with cycle conditions, 40 cycles: 94° C., 15 s; 56° C., 30 s and 72° C., 30 s, followed by a final 72° C. extension for 3 min. Analysis of relative gene expression data was performed using the ΔΔCt method. A plot of the log cDNA dilution versus ΔCt was generated for each target gene tested to validate the qPCR experiments. The slopes of regression lines for neuromacin and Hm-lumbricin were 0.0698 and 0.0864 respectively suggesting equivalent efficiencies of amplification (data not shown) (Livak, K. J., 2001 Methods 25:402-408).

In situ hybridization: Microglia deficient nerve cords were fixed in a solution containing 4% paraformaldehyde at 4° C. overnight. Plasmids containing the coding region of neuromacin and Hm-lumbricin probes were used as templates for the synthesis of the probes. Digoxigenin (DIG)-UTP-labeled antisense and sense riboprobes were generated from linearized cDNA plasmids by in vitro transcription using RNA-labeling-kit (Roche™). DIG-labeled riboprobes (40-100 ng per slide) were hybridized as previously described (Tasiemski, A., 2004, J Biol Chem 279:30973-30982). Slides were observed under a Zeiss™ Axioskop microscope. As a control, antisense riboprobes were replaced by sense riboprobes.

Single cell RT-PCR: Single cell RT-PCRs were carried out on fresh dissociated neurons and microglial cells. Cells were individually collected using a patch-clamp micromanipulator (Roudbaraki, M., A. et al 1999 Endocrinology 140:4874-4885). Patch pipettes were filled with the internal pipette solution (10 µl of 140 mM KCl, 2 mM $MgCl_2$, 1.1 mM EGTA and 10 mM Eepes, pE 7.25). Neurons and microglial cells were aspired under visual control. The pipette content (~8 µl) was ejected into a 0.2 ml PCR microtube without touching the wall, immediately frozen with nitrogen azote and kept at −80° C. until use. A new patch pipette was used for each new collection. The RT reaction was performed with one single cell using oligodT(18) primer according to Roudbaraki et al (1999, cited above) The following sense primers were designed to amplify with an oligodT(34) primer cgagtcgacatcgatcg(t)$_{18}$ (SEQ ID NO: 18) a PCR size product under 500 bp: Neuromacin: 5'-ctcttctcaacaagttgctctgc-3' (SEQ ID NO: 35) and Hm-lumbricin: 5'-cagcaagtacgagaggcaaaaggaca-3' (SEQ ID NO: 36)

PCR was performed by using 4 µl RT template according to the protocol of the AmpliTaq Gold (Applied Biosystems). The conditions of DNA amplification included an initial denaturation step of 10 min at 95° C., 45 cycles of 45 s at 95° C., 45 s at 60 C, and 45 s at 72° C.; and finally 5 min at 72° C. The PCR products were loaded onto a 1% agarose gel.

Immunohistochemical and Immunocytochemical Procedures

Polyclonal antisera: Because of the high conservation between neuromacin and theromacin epitopes, the theromacin antiserum was used for our analysis. This rabbit antibody recognizes a synthetic peptide corresponding to theromacin ($Gln_{49}$-$Arg_{63}$) as previously described (Tasiemski 2004 cited above). The Hm-lumbricin antiserum was produced in the laboratory. The chemically synthesized region of Hm-lumbricin ($Gln_5$-$Pro_{30}$) was coupled to ovalbumin and used for the immunization procedure of two New Zealand White rabbits (Saprophyte Pathogen free) according to the protocol previously described (Baert, J. L., M. et al. 1991, Eur J Biochem 201:191-198).

Whole mount immunohistochemistry: Nerve cords depleted or not of microglial cells were fixed overnight at 4° C. in 4% paraformaldehyde at different times after bacterial exposure. Membranes were permeabilized by incubating the samples in PBS containing 1% Triton X-100 for 24 h at room temperature. Non-specific background staining was blocked with a PBS solution containing 1% Triton, 3% normal goat serum (NGS) and 1% ovalbumin for 8 h at room temperature. Samples were then incubated with whether rabbit neuromacin antibodies (1:800) or rabbit Hm-lumbricin antibodies (1:200) diluted in the AB solution (PBS containing 1% BSA 0.05% Triton 1% NGS 1% NDS 1% Ovalbumin) overnight at 4° C. Primary antibodies were removed and samples were incubated with Alexa Fluor 546 conjugated to goat anti-rabbit secondary antibody (Invitrogen) diluted 1:4000 in the AB solution. As a control, the immunolabeling procedure was carried out with the preimmune serum. Slides were mounted and examined using a confocal microscope (Zeiss LSM 510) or an inverted microscope (Leica DMIRE2).

Immunocytochemistry: Neurons dissociated from nerve cords incubated for 6 hours with bacteria were fixed for 30 min at 4° C. by addition of ice-cold 4% paraformaldehyde solution.

Cells were then centrifuged on slides (12,000 neurons/slide) and immersed for 10 minutes in Tris-buffered saline (TBS; 0.1 mol/L Tris, pH 7.5 or less, 0.9% NaCl). After 1 hour of incubation in TBS containing 3% normal goat serum (NGS), cells were incubated overnight at 20° C. with rabbit anti-lumbricin antibodies (1/100) or anti-neuromacin antibodies (1/400) in TBS containing 2% NSG and 0.01% Triton X-100. Next, cells were rinsed 3 times with TBS and incubated for 2 hours at room temperature with FITC-conjugated goat antirabbit IgG diluted 1/100 (Jackson Immunoresearch). Cells were examined using a confocal microscope (Zeiss LSM 510).

Results

More successful regeneration of the leech CNS under septic than under sterile conditions Sectioning of one side of the paired connective nerve linking adjacent segmental ganglia was performed on excised nerve cords maintained in culture (shown schematically in FIG. 1A). To monitor the progress of nerve repair, micrographs of the damaged nerve cords were taken every 24 h, in the presence or absence of bacteria. Under sterile conditions, as documented in FIG. 1B, restoration of the connective nerve across the cut begins at ~4 days post-axotomy (panel J4) and is finished 4 days later. This is in line with the observations reported by Müller et al (Muller, K. J., et al. 1979. J Comp Neurol 185:485-516.22), who demonstrated that even the synaptic connections and normal functions of axotomized leech neurons were restored after 8 days. In comparison, nerve repair is evident sooner in the presence of bacteria, reconnection starting after 2 days or 3 days with live or heat-killed bacteria (FIGS. 1C and 1D). In the case of incubation with live bacteria, however, signs of degeneration are soon present (FIG. 1C, panel J4), probably as a consequence of the uncontrollable expansion of the bacterial population in the rich culture medium, which becomes deleterious for the CNS. By contrast, incubation with a defined amount of heat-killed bacteria appears to promote the regeneration process relative to sterile conditions.

Purification and Molecular Characterization of Antimicrobial Peptides Produced by the Leech CNS Neuromacin and Hm-lumbricin were isolated from a preparation of 100 nerve cords of *Hirudo medicinalis* under acidic conditions (FIG. 2). Identification and characterization of both molecules were performed by combining N-terminal sequencing by Edman degradation, MALDI-TOF mass spectrometry and cDNA cloning (FIG. 3) Amino acid sequences deduced from the cDNAs allowed the conclusion that neuromacin and Hm-lumbricin are both cationic peptides with calculated pI of 8.49 and 9.16, respectively. Data bank analysis (BLAST program in Swiss-Prot) revealed that the primary structure of neuromacin was 67% identical to that of theromacin, an antibacterial peptide previously isolated by our group from the body fluid of the leech *Theromyzon tessulatum* (19). Neuromacin was named according to its apparent homology to theromacin and its production being restricted to the nervous system. Searches in databases from Genbank and EST libraries revealed the presence of putative neuromacin-like gene products, often named theromacin-like in various invertebrate species such as the mollusks *Aplysia californica* and *Biomphalaria glabrata* and the annelid *Lumbricus rubellus* (FIG. 4A).

Blast analysis results (FIG. 4B) show that Hm-lumbricin shares 78% sequence identity with lumbricin-1, an antimicrobial peptide originally isolated from the earthworm *Lumbricus rubellus*, and 81% sequence identity with PP-1, a lumbricin-1-like gene product cloned from another earthworm, *Pheretima tschiliensis* (Cho, J. H. et al 1998. *Biochim Biophys Acta* 1408:67-76; Wang, X., X., 2003. *Biotechnol Lett* 25:1317-1323).

Biological Activity of Neuromacin and Hm-Lumbricin

In liquid growth inhibition assay, the purified neuromacin was active against *Micrococcus nishinomiyaensis* (MIC 1.95-3.8 µM; MBC 7.8-15.6 µM). No activity was found towards the Gram negative *A. hydrophila* at the same concentration. To investigate the mode of action of neuromacin against Gram positive bacteria, we used *B. megaterium* and the fluorescent dye SYTOX Green. Results of this assay demonstrate that neuromacin rapidly permeabilizes bacterial membranes and is thus potently active against these Gram-positives (FIG. 5A). Since neuromacin contains four histidine residues in its primary structure (in contrast to none in theromacin), we evaluated the effect of a more acidic pH, at which the histidine residues are protonated, on the membrane-permeabilizing activity (FIG. 5B). The efficacy of neuromacin to induce membrane lesions in viable bacteria was found to be weaker at pH 5.2 than at pH 7.4. Within the measurement period, the activity of neuromacin against the target bacterium tested appeared to be over one order of magnitude lower than those for the well-known antimicrobial peptides cecropin P1 and magainin II. Similar activity against the Gram-negative representative *E. coli* was not detected up to a neuromacin concentration of 25 µM (data not shown). We also measured the pore-forming activity of neuromacin to further characterize its mode of action by using a minimalistic membrane system. More precisely, we monitored the dissipation of a membrane potential induced in liposomes composed of azolectin, a crude phospholipid mixture from soy bean. Pore-forming activity was not detected at final concentrations up to 2 µM, whereas the positive control alamethicin gave a very strong signal at 50 nM (data not shown).

Based on the amino acid homologies with lumbricin-1 (FIG. 4B), we speculate that Hm-lumbricin and lumbricin-1 must have similar antimicrobial properties. Notably, the N-terminal sequence, which is the most conserved part between lumbricin 1 and Hm-lumbricin, has been shown by Cho et al to exhibit a stronger activity than the entire lumbricin-1 against fungi, Gram positive and Gram negative bacteria, without exerting any hemolytic activities (Cho, 1998 cited above).

The capacity of both peptides to promote the regeneration of the leech nerve cord was also tested ex vivo by adding the neuromacin and/or Hm-lumbricin antibody (ies) to axotomized nerve cords in presence of killed bacteria (FIG. 6). Due to the presence of bacteria, the reconnection process should have started 3 days post-axotomy (FIG. 1D). It appeared that the presence of antibodies in the culture medium blocked the regeneration process since no reconnection was observed even 7 days post-axotomy. That suggests that both peptides are involved in the regenerative process of the leech CNS. These observations were corroborated by the data obtained by adding native neuromacin to axotomized nerve cords under aseptic conditions (FIG. 6). Nerve repair was evident sooner in the presence of neuromacin, reconnection starting in less than 24 hours instead of 4 days without neuromacin. So, in addition to exerting antimicrobial properties, Hm-lumbricin and neuromacin have the capacity to enhance the regenerative responses of the leech CNS.

Synthesis of Antimicrobial Peptides by Neurons and by Microglial Cells

Gene expression sites of neuromacin and Hm-lumbricin were investigated by single cell RT-PCR and by ISH (FIG. 7). Interestingly, both genes are expressed in neurons after septic exposure of the CNS. This is the first reported observation of the transcription of antimicrobial peptides by neurons in an invertebrate. Neuromacin and at a lower level Hm-lumbricin transcripts were also detected in microglial cells.

Specific Induction of Antimicrobial Peptides Genes in the Leech CNS

Gene expression patterns of neuromacin and Hm-lumbricin during an induced immune response were investigated by real time PCR. As illustrated in FIGS. 8A and 8B, neuromacin and Hm-lumbricin transcript levels were rapidly enhanced by bacterial challenge, but no significant changes were measured following axotomy under sterile conditions, indicating that the induction was not due to the axotomy itself, but rather to the incubation of the nerve cords with bacteria.

We have further attempted to analyze whether the leech nervous system was able to discriminate among different microorganisms. The data presented in FIG. 8B indicate that treatment of the nerve cord with the gram positive bacterium *M. nishinomiyaensis* induces an increase in both Hm-lumbricin and neuromacin mRNA levels, the first more pronounced than the second. In contrast, no significant change in neuromacin expression but a large increase in the level of Hm-lumbricin transcripts was observed following challenge with zymosan, a component of yeast membrane. This distinct pattern of induction appears to correlate with the activity of the peptides encoded by these genes. Indeed, the neuromacin gene, which encodes a product with anti-Gram positive activity, is induced by Gram positive bacteria, and the Hm-lumbricin gene, which encodes an anti-Gram positive and anti-fungal peptide, is induced by both Gram positives and zymosan. These results suggest that the leech CNS responds to infection with a pathogen-specific pattern of gene expression.

Accumulation of Antimicrobial Peptides at the Site of Axotomy

To get further information on possible roles of both antimicrobial peptides in the immune response of the leech CNS, double staining was performed on challenged nerve cords at t=0 h and t=6 h post-axotomy by using Hoechst 33258 and either the anti-Hm-lumbricin polyclonal antibody or the anti-neuromacin polyclonal antibody (FIG. 9). Challenge with *M. nishinomiyaensis* was chosen because of its efficacy to induce the expression of both Hm-lumbricin and neuromacin genes. By contrast with the CNS fixed immediately after dissection (FIGS. 9A, B), nerve cords fixed 6 h after septic challenge present a strong immunoreactivity with both antibodies at the lesion (FIGS. 9E, F), along with an accumulation of microglial cells as revealed by nuclear staining with Hoechst 33258 (FIGS. 9G, H). Microglial cells are resident cells evenly distributed in leech ganglia and in the bundle of axons that connect them. After damage to the CNS, these cells have been shown by Müller and co-workers to migrate to the site of the lesion, where they accumulate (Morgese, V. J. et al., 1983. *Brain Res* 272:166-170). There, microglial cells phagocytose damaged tissue and produced laminin, an extracellular matrix molecule known to promote neurite outgrowth in the leech and in vertebrates Immunolocalization of both peptides at the axotomized site where microglial cells accumulate suggests a production and a release of Hm-lumbricin and neuromacin by these cells. Six hours post-challenge, neuromacin but not Hm-lumbricin was also strongly immunolocalized in microglial cells covering the segmental ganglia and the connectives (insets FIG. 9E). It has been shown that nearly all microglial cells are able to move, but that after the cord has been crushed, only 15-40% of them migrate to the injured site. We hypothesize that the induction of neuromacin synthesis is relevant to the global population of microglial cells, whereas the induction of Hm-lumbricin synthesis only pertains to the cells recruited to the lesion site.

Interestingly, ISH combined with single cell RT-PCR demonstrated the presence of neuromacin and Hm-lumbricin mRNAs in neurons (FIG. 7). In order to determine whether the detection of both peptides at the lesion site could also reflect a neuronal production, we have developed an ex vivo model of leech CNS almost completely devoid of microglial cells. Each segmental ganglion of the medicinal leech nerve cord is enclosed in a capsule. As revealed by nuclear staining with Hoechst 33258 (FIGS. 10G and 10H), mechanical destruction of the capsule resulted in a marked reduction, within 6 hours, in the numbers of microglial cells surrounding the nerve cord. With these conditions, the accumulation of microglial cells which is normally observable (FIGS. 9G, 9H) at the axotomized site does not occur anymore to (FIGS. 10G and 10H). As presented in FIGS. 10E and 10F, it appeared that this depletion does not affect the accumulation of both peptides at the site of axotomy. Confocal microscopy analysis (insets FIGS. 10E and 10F) more precisely evidenced the presence of Hm-lumbricin and neuromacin in the cell body of neurons and in the axons of the injured connectives, suggesting a neuronal production presumably followed by the axonal transport of the antimicrobial peptides to the lesion site. Thus, the presence of both Hm-lumbricin and neuromacin at the axotomized site implicates peptide production by neurons and by the microglial cells recruited at the lesion site.

Hm-Lumbricin Exocytosis

Precursor sequences were also deduced from the cDNA sequences (FIG. 3). Signal PVI software analysis revealed that the N-terminal Asp of neuromacin is preceded by a putative signal peptide comprising $Met_1$-$Pro_{23}$ (FIG. 3A). This leads to the notion that neuromacin may be generated through conventional processing mechanisms and can be secreted to the extracellular medium. By contrast, Hm-lumbricin precursor lacks a typical signal sequence making its extracellular presence unlikely. In order to determine whether Hm-lumbricin could be released upon microbial stimulation, peptide purification was investigated from the incubation medium of nerve cords challenged with zymosan (FIG. 11). Zymosan was chosen because of its specificity and efficiency to induce the expression of the gene encoding Hm-lumbricin (FIG. 8B). RP-HPLC analysis coupled to DIA evidenced the presence of Hm-lumbricin in the culture medium demonstrating that despite lacking a signal peptide, this antimicrobial peptide can be secreted and so can exert its biological effects. It is noteworthy that several molecules devoid of a signal peptide have been shown to be secreted. For example, PP1, a lumbricin-like peptide found in *P. tschiliensis*, has been detected in the mucus it secretes (23). In vertebrates, the rat PEBP was shown to be secreted into epididymal fluid despite lacking a signal peptide (Jones, R., et al 1991. *Biochim Biophys Acta* 1080:78-82).

The invention claimed is:

1. A purified peptide having antimicrobial and neurotrophic activity, said peptide comprising the amino acid sequence of SEQ ID NO: 28.

2. A purified peptide having antimicrobial and neurotrophic activity, said peptide consisting of the amino acid sequence of SEQ ID NO: 28.

3. A composition comprising the peptide of SEQ ID NO:28, and a pharmaceutically acceptable excipient and/or carrier.

* * * * *

SEQUENCE LISTING

```
<160> NUMBER OF SEQ ID NOS: 38

<210> SEQ ID NO 1
<211> LENGTH: 418
<212> TYPE: DNA
<213> ORGANISM: Hirudo medicinalis
<220> FEATURE:
<221> NAME/KEY: CDS
<222> LOCATION: (1)..(246)

<400> SEQUENCE: 1 atg gct ctt ctc aac aag ttg ctc tgc ttt gct ctg gtc ttc atg atc      48
Met Ala Leu Leu Asn Lys Leu Leu Cys Phe Ala Leu Val Phe Met Ile
1               5                   10                  15 ttc ggt gag ttc gtg act ccg gat tgc tac gag gac tgg agc agg tgc      96
Phe Gly Glu Phe Val Thr Pro Asp Cys Tyr Glu Asp Trp Ser Arg Cys
                20                  25                  30 acg cct gga acg tca ttc ctg act gga atc ctg tgg aaa gat tgc cac     144
Thr Pro Gly Thr Ser Phe Leu Thr Gly Ile Leu Trp Lys Asp Cys His
            35                  40                  45
```

```
agc cgt tgc aag gaa ctc ggt cac agg gga gga cga tgt gtg gat tca      192
Ser Arg Cys Lys Glu Leu Gly His Arg Gly Gly Arg Cys Val Asp Ser
 50                  55                  60 cca agc aaa cac tgc cct gga gtc ctc aag aac aac aaa cag tgt cat      240
Pro Ser Lys His Cys Pro Gly Val Leu Lys Asn Asn Lys Gln Cys His
 65                  70                  75                  80 tgc tac tgatctgaag aattgttgaa atatgttgga gattctggaa ggacagtgac       296
Cys Tyr catgatttgt gattttcttt aaaaatcact tagttaagta aaacattgg cgatgattac      356 gcttacataa taaagtatta ttttgcgatt gcaccattcc aaaaaaaaaa aaaaaaaaa      416 aa                                                                    418

<210> SEQ ID NO 2
<211> LENGTH: 82
<212> TYPE: PRT
<213> ORGANISM: Hirudo medicinalis

<400> SEQUENCE: 2

Met Ala Leu Leu Asn Lys Leu Leu Cys Phe Ala Leu Val Phe Met Ile
  1               5                  10                  15

Phe Gly Glu Phe Val Thr Pro Asp Cys Tyr Glu Asp Trp Ser Arg Cys
                 20                  25                  30

Thr Pro Gly Thr Ser Phe Leu Thr Gly Ile Leu Trp Lys Asp Cys His
             35                  40                  45

Ser Arg Cys Lys Glu Leu Gly His Arg Gly Gly Arg Cys Val Asp Ser
 50                  55                  60

Pro Ser Lys His Cys Pro Gly Val Leu Lys Asn Asn Lys Gln Cys His
 65                  70                  75                  80

Cys Tyr

<210> SEQ ID NO 3
<211> LENGTH: 414
<212> TYPE: DNA
<213> ORGANISM: Hirudo medicinalis
<220> FEATURE:
<221> NAME/KEY: CDS
<222> LOCATION: (1)..(171)

<400> SEQUENCE: 3 atg ttc agc aag tac gag agg caa aag gac aaa aga agt tac ggt gaa       48
Met Phe Ser Lys Tyr Glu Arg Gln Lys Asp Lys Arg Ser Tyr Gly Glu
  1               5                  10                  15 agg ttc agc atg ttc aca ggc cct cag ttc att tcg ccc ccc gag agg       96
Arg Phe Ser Met Phe Thr Gly Pro Gln Phe Ile Ser Pro Pro Glu Arg
                 20                  25                  30 atc aaa ccc aac aaa att ctc cag tgg gat ggg gag ggc atg ccc att      144
Ile Lys Pro Asn Lys Ile Leu Gln Trp Asp Gly Glu Gly Met Pro Ile
             35                  40                  45 tac gcc acg tcg ggg gct gca gcc gag taaggagagc cgattggcga            191
Tyr Ala Thr Ser Gly Ala Ala Ala Glu
 50                  55 ctgaccagcc aatatgacca ggcaatgaca agccaggata ttttggagt aattcgacat     251 tcagagacgg tccttaaaat gtctccaatg atttgtggaa tcgattcgag ttttgaatta    311
aacgatatct caataaaata tcggttaaat ttttgcaatt tcgtcaccaa atattaatgt    371
caaataaata gttctttcta aagcgaaaaa aaaaaaaaa aaa                       414

<210> SEQ ID NO 4
<211> LENGTH: 57
```

```
<212> TYPE: PRT
<213> ORGANISM: Hirudo medicinalis

<400> SEQUENCE: 4

Met Phe Ser Lys Tyr Glu Arg Gln Lys Asp Lys Arg Ser Tyr Gly Glu
1               5                   10                  15

Arg Phe Ser Met Phe Thr Gly Pro Gln Phe Ile Ser Pro Pro Glu Arg
                20                  25                  30

Ile Lys Pro Asn Lys Ile Leu Gln Trp Asp Gly Glu Gly Met Pro Ile
            35                  40                  45

Tyr Ala Thr Ser Gly Ala Ala Ala Glu
        50                  55

<210> SEQ ID NO 5
<211> LENGTH: 398
<212> TYPE: DNA
<213> ORGANISM: Theromyzon tessulatum
<220> FEATURE:
<221> NAME/KEY: CDS
<222> LOCATION: (1)..(294)

<400> SEQUENCE: 5 atg gaa ttg aaa tct ggt ctc agt att ttg ttg tgc ttt ggg atc tgc      48
Met Glu Leu Lys Ser Gly Leu Ser Ile Leu Leu Cys Phe Gly Ile Cys
1               5                   10                  15 att gca gtg att aat gcg gga tgt ttc gaa gat tgg agt cgt tgt tcg      96
Ile Ala Val Ile Asn Ala Gly Cys Phe Glu Asp Trp Ser Arg Cys Ser
                20                  25                  30 cca tcg acg tct cgt gga aca gga gtt tta tgg aga gat tgt gac agt     144
Pro Ser Thr Ser Arg Gly Thr Gly Val Leu Trp Arg Asp Cys Asp Ser
            35                  40                  45 tac tgc aaa gtt tgt ttc aaa gct gat agg gga gaa tgt ttt gat tca     192
Tyr Cys Lys Val Cys Phe Lys Ala Asp Arg Gly Glu Cys Phe Asp Ser
50                  55                  60 cca agt cta aat tgt cca caa cgt cta cca aat aac aaa caa tgc agg     240
Pro Ser Leu Asn Cys Pro Gln Arg Leu Pro Asn Asn Lys Gln Cys Arg
65                  70                  75                  80 tgc ata aac gct aga act gca aaa gac aat agg aat cca act tgt tgg     288
Cys Ile Asn Ala Arg Thr Ala Lys Asp Asn Arg Asn Pro Thr Cys Trp
                85                  90                  95 gct taa ctttaatcag aaaaaaacaa tgcttttata atttattttg ttaaactttta     344
Ala ttgcgctcat ttttatctg aaataaaac atgtatgaat taaaaaaaaa aaaa           398

<210> SEQ ID NO 6
<211> LENGTH: 97
<212> TYPE: PRT
<213> ORGANISM: Theromyzon tessulatum

<400> SEQUENCE: 6

Met Glu Leu Lys Ser Gly Leu Ser Ile Leu Leu Cys Phe Gly Ile Cys
1               5                   10                  15

Ile Ala Val Ile Asn Ala Gly Cys Phe Glu Asp Trp Ser Arg Cys Ser
                20                  25                  30

Pro Ser Thr Ser Arg Gly Thr Gly Val Leu Trp Arg Asp Cys Asp Ser
            35                  40                  45

Tyr Cys Lys Val Cys Phe Lys Ala Asp Arg Gly Glu Cys Phe Asp Ser
        50                  55                  60

Pro Ser Leu Asn Cys Pro Gln Arg Leu Pro Asn Asn Lys Gln Cys Arg
65                  70                  75                  80
```

```
Cys Ile Asn Ala Arg Thr Ala Lys Asp Asn Arg Asn Pro Thr Cys Trp
                85                  90                  95
Ala

<210> SEQ ID NO 7
<211> LENGTH: 225
<212> TYPE: DNA
<213> ORGANISM: Hirudo medicinalis
<220> FEATURE:
<221> NAME/KEY: CDS
<222> LOCATION: (1)..(225)

<400> SEQUENCE: 7 tgt ttc gaa gat tgg agt cgt tgt tcg cca tcg aca gct agt gca aca        48
Cys Phe Glu Asp Trp Ser Arg Cys Ser Pro Ser Thr Ala Ser Ala Thr
1               5                   10                  15 gga gtt tta tgg aga agt tgt gac agt tac tgc aaa gtt tgt ttc aaa        96
Gly Val Leu Trp Arg Ser Cys Asp Ser Tyr Cys Lys Val Cys Phe Lys
            20                  25                  30 gct gat agg gga gaa tgt tat gat tcg cca agt ctc aat tgt cca cat       144
Ala Asp Arg Gly Glu Cys Tyr Asp Ser Pro Ser Leu Asn Cys Pro His
        35                  40                  45 cgt cta cca aat aac aaa caa tgc agg tgc ata aac gct aga act gca       192
Arg Leu Pro Asn Asn Lys Gln Cys Arg Cys Ile Asn Ala Arg Thr Ala
    50                  55                  60 aaa gac aat agg aat cca act tgt tgg gct tga                           225
Lys Asp Asn Arg Asn Pro Thr Cys Trp Ala
65                  70

<210> SEQ ID NO 8
<211> LENGTH: 74
<212> TYPE: PRT
<213> ORGANISM: Hirudo medicinalis

<400> SEQUENCE: 8

Cys Phe Glu Asp Trp Ser Arg Cys Ser Pro Ser Thr Ala Ser Ala Thr
1               5                   10                  15

Gly Val Leu Trp Arg Ser Cys Asp Ser Tyr Cys Lys Val Cys Phe Lys
            20                  25                  30

Ala Asp Arg Gly Glu Cys Tyr Asp Ser Pro Ser Leu Asn Cys Pro His
        35                  40                  45

Arg Leu Pro Asn Asn Lys Gln Cys Arg Cys Ile Asn Ala Arg Thr Ala
    50                  55                  60

Lys Asp Asn Arg Asn Pro Thr Cys Trp Ala
65                  70

<210> SEQ ID NO 9
<211> LENGTH: 633
<212> TYPE: DNA
<213> ORGANISM: Aplysia californica
<220> FEATURE:
<221> NAME/KEY: CDS
<222> LOCATION: (200)..(430)

<400> SEQUENCE: 9
ggctcgagcg gctcgagtga cgccagcact agatctatat gtatccaaca aagtctcgac        60
atcttgcagt tgcagttccc caagaaggcc tatttaatcg acggttggaa cttttccttc       120
cgcccagctc cttgaaaaga ggcagccagg gaacataaca agaagattgt cattagaaac       180
tgctgggaca cttggcacg atg gac aag aag gca gca aat gga gga aaa gag       232
                       Met Asp Lys Lys Ala Ala Asn Gly Gly Lys Glu
                       1               5                   10
```

```
aag ggc ccc ttg gaa gcc tgc tgg gac gag tgg agc aga tgt aca ggt      280
Lys Gly Pro Leu Glu Ala Cys Trp Asp Glu Trp Ser Arg Cys Thr Gly
            15                  20                  25 tgg agc tct gct ggc act gga gtt ctt tgg aaa tct tgt gat gac cag      328
Trp Ser Ser Ala Gly Thr Gly Val Leu Trp Lys Ser Cys Asp Asp Gln
        30                  35                  40 tgc aaa aag ctg ggg aaa agc ggt gga gaa tgt gtg ctc act ccc tct      376
Cys Lys Lys Leu Gly Lys Ser Gly Gly Glu Cys Val Leu Thr Pro Ser
45                  50                  55 act tgc cca ttt aca cgt acc gac aag gct tac caa tgc cag tgc aag      424
Thr Cys Pro Phe Thr Arg Thr Asp Lys Ala Tyr Gln Cys Gln Cys Lys
60                  65                  70                  75 aag taa agttttacac aggagctgac gcgtccacga ttatctactt cgtcgggacc      480
Lys acatctagtg aggcaattgg tgcaaacata ttgacatagg tttattcttt ccgggaactc      540
agaaattcag aattttgaag tttaattaag taaacaacac gttagataat gggatttcaa      600
aaataaagat gaaattatga agttttaaaa aaa                                  633

<210> SEQ ID NO 10
<211> LENGTH: 76
<212> TYPE: PRT
<213> ORGANISM: Aplysia californica

<400> SEQUENCE: 10

Met Asp Lys Lys Ala Ala Asn Gly Gly Lys Glu Lys Gly Pro Leu Glu
1               5                   10                  15

Ala Cys Trp Asp Glu Trp Ser Arg Cys Thr Gly Trp Ser Ser Ala Gly
            20                  25                  30

Thr Gly Val Leu Trp Lys Ser Cys Asp Asp Gln Cys Lys Lys Leu Gly
        35                  40                  45

Lys Ser Gly Gly Glu Cys Val Leu Thr Pro Ser Thr Cys Pro Phe Thr
    50                  55                  60

Arg Thr Asp Lys Ala Tyr Gln Cys Gln Cys Lys Lys
65                  70                  75

<210> SEQ ID NO 11
<211> LENGTH: 555
<212> TYPE: DNA
<213> ORGANISM: Lumbricus rubellus
<220> FEATURE:
<221> NAME/KEY: CDS
<222> LOCATION: (84)..(314)

<400> SEQUENCE: 11
ggcacgagct atctctctgc ctcatcactc tcccttrccc ctctctctct ctcattatct      60
tgctgtctct ctgtctgact atc atg tct ctc tgt atc tct gac tat ctc tat      113
                        Met Ser Leu Cys Ile Ser Asp Tyr Leu Tyr
                          1               5                   10 ctg act ctg act ttc tca aag tac gaa cgc cag aag gac aag agg cca      161
Leu Thr Leu Thr Phe Ser Lys Tyr Glu Arg Gln Lys Asp Lys Arg Pro
                15                  20                  25 tac tcg gaa cgc aag aac caa tac acg ggt ccg cag ttc ctc tat cct      209
Tyr Ser Glu Arg Lys Asn Gln Tyr Thr Gly Pro Gln Phe Leu Tyr Pro
        30                  35                  40 ccg gag cgc atc cca ccg cag aag gtc atc aaa tgg aac gag gag ggt      257
Pro Glu Arg Ile Pro Pro Gln Lys Val Ile Lys Trp Asn Glu Glu Gly
    45                  50                  55 ctt ccc atc tac gaa atc ccc ggc gaa gga ggt cac gca gaa cca gct      305
Leu Pro Ile Tyr Glu Ile Pro Gly Glu Gly Gly His Ala Glu Pro Ala
60                  65                  70
```

```
gcc gcc tag gttagatttc agctgaaccg attgccaacc ggagaggaag              354
Ala Ala
 75 agagttgatt tcgatagagc gtgtggacag aactatcagc gttctttta ccatcgtcgc    414 tataagtcta tcactcttag aggatcaagt agattgcgta gacctagtta actaaaccta   474 aatcaattgt tgtcttggtt ttaaatgagt ggagaggaaa attaaacaaa ttacaacccc   534 taaaaaaaaa aaaaaaaaa a                                               555

<210> SEQ ID NO 12
<211> LENGTH: 76
<212> TYPE: PRT
<213> ORGANISM: Lumbricus rubellus

<400> SEQUENCE: 12

Met Ser Leu Cys Ile Ser Asp Tyr Leu Tyr Leu Thr Leu Thr Phe Ser
1               5                   10                  15

Lys Tyr Glu Arg Gln Lys Asp Lys Arg Pro Tyr Ser Glu Arg Lys Asn
            20                  25                  30

Gln Tyr Thr Gly Pro Gln Phe Leu Tyr Pro Pro Glu Arg Ile Pro Pro
        35                  40                  45

Gln Lys Val Ile Lys Trp Asn Glu Glu Gly Leu Pro Ile Tyr Glu Ile
    50                  55                  60

Pro Gly Glu Gly Gly His Ala Glu Pro Ala Ala Ala
65                  70                  75

<210> SEQ ID NO 13
<211> LENGTH: 622
<212> TYPE: DNA
<213> ORGANISM: Pheretima tschiliensis
<220> FEATURE:
<221> NAME/KEY: CDS
<222> LOCATION: (43)..(246)

<400> SEQUENCE: 13
aaaattcagg agcgctttgc aggaactccg gcaaagatcg ag atg tac agc aag      54
                                              Met Tyr Ser Lys
                                              1 tac gag aga cag aag gac aag aga ccg tac tcg gag cgg aag gac cag    102
Tyr Glu Arg Gln Lys Asp Lys Arg Pro Tyr Ser Glu Arg Lys Asp Gln
5                   10                  15                  20 tac acc gga ccg cag ttc ctc tat ccg ccc gat cgc atc ccg ccg agc    150
Tyr Thr Gly Pro Gln Phe Leu Tyr Pro Pro Asp Arg Ile Pro Pro Ser
                25                  30                  35 aaa gcc atc aaa tgg aac gaa gag ggc ctt ccg atg tac gag gtc ctc    198
Lys Ala Ile Lys Trp Asn Glu Glu Gly Leu Pro Met Tyr Glu Val Leu
            40                  45                  50 ccg gac gga gca ggg gca aag acc gcc gtt gag gcc gcc gct gaa tag   246
Pro Asp Gly Ala Gly Ala Lys Thr Ala Val Glu Ala Ala Ala Glu
        55                  60                  65 aatatttgac cgattaaacg ctctagacat tcggatgatt tgagatgcaa catgacgcct   306
gcgatcacag agtgaccttg acagtaacct ttcgtaggaa ccgacaaatc gctgctaata   366
aacactggcg cctcataaat tctaaaatcc tgagtagaaa ccgatgtaat ctagtggctc   426
cgttcgatta gtttagcaat tactttagcg cacttatctg aatgccgtca gtcgatggaa   486
caaattagtt gattttgcag atttctaaga acaacaacga agtcgatttc tgtatcggaa   546
ttacccttga tctatttaga acagccactg cctctaattc gagaattcaa taaaatccag   606
cagttttagc agaatg                                                    622
```

<210> SEQ ID NO 14
<211> LENGTH: 67
<212> TYPE: PRT
<213> ORGANISM: Pheretima tschiliensis

<400> SEQUENCE: 14

Met Tyr Ser Lys Tyr Glu Arg Gln Lys Asp Lys Arg Pro Tyr Ser Glu
1               5                   10                  15

Arg Lys Asp Gln Tyr Thr Gly Pro Gln Phe Leu Tyr Pro Pro Asp Arg
            20                  25                  30

Ile Pro Pro Ser Lys Ala Ile Lys Trp Asn Glu Glu Gly Leu Pro Met
        35                  40                  45

Tyr Glu Val Leu Pro Asp Gly Ala Gly Ala Lys Thr Ala Val Glu Ala
    50                  55                  60

Ala Ala Glu
65

<210> SEQ ID NO 15
<211> LENGTH: 57
<212> TYPE: PRT
<213> ORGANISM: Lumbricus rubellus

<400> SEQUENCE: 15

Gly Cys Tyr Glu Asp Trp Ser Arg Cys Thr Pro Ser Thr Ser Trp Leu
1               5                   10                  15

Thr Gly Ile Leu Trp Lys Ser Cys Thr Asn Arg Cys Lys Glu Gln Gly
            20                  25                  30

His Arg Gly Gly Asn Cys Arg Asp Ser Pro Ser Pro Cys Pro Gly Leu
        35                  40                  45

Gln Asn Asn Lys Gln Cys Tyr Cys Phe
    50                  55

<210> SEQ ID NO 16
<211> LENGTH: 62
<212> TYPE: PRT
<213> ORGANISM: Biomphalaria glabrata

<400> SEQUENCE: 16

Asn Val Ile Gly Arg Cys Trp Asp Thr Trp Ser Arg Cys Ser Thr Trp
1               5                   10                  15

Ser Arg Trp Phe Thr Gly Arg Val Trp Leu Thr Arg Asp Gly Lys Cys
            20                  25                  30

Arg Glu Leu Gly Lys Arg Gly Gly Asn Cys Val Met Thr Pro Ser Thr
        35                  40                  45

Cys Pro Leu Ser Ser Glu Ala Phe Gln Cys Gln Cys Tyr Thr
    50                  55                  60

<210> SEQ ID NO 17
<211> LENGTH: 25
<212> TYPE: DNA
<213> ORGANISM: Artificial Sequence
<220> FEATURE:
<223> OTHER INFORMATION: Synthetic primer

<400> SEQUENCE: 17
atggaggagg aaattgaaga actcc                                         25

<210> SEQ ID NO 18
<211> LENGTH: 35
<212> TYPE: DNA

```
<213> ORGANISM: Artificial Sequence
<220> FEATURE:
<223> OTHER INFORMATION: Synthetic primer

<400> SEQUENCE: 18
cgagtcgaca tcgatcgttt tttttttttt ttttt                             35

<210> SEQ ID NO 19
<211> LENGTH: 18
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n= C or T
<220> FEATURE:
<221> NAME/KEY: misc_feature
<222> LOCATION: (6)..(6)
<223> OTHER INFORMATION: n= C or T
<220> FEATURE:
<221> NAME/KEY: misc_feature
<222> LOCATION: (9)..(9)
<223> OTHER INFORMATION: n= C or T
<220> FEATURE:
<221> NAME/KEY: misc_feature
<222> LOCATION: (12)..(12)
<223> OTHER INFORMATION: n= A or G
<220> FEATURE:
<221> NAME/KEY: misc_feature
<222> LOCATION: (15)..(15)
<223> OTHER INFORMATION: n= C or T

<400> SEQUENCE: 19
gantgntang angantgg                                                18

<210> SEQ ID NO 20
<211> LENGTH: 24
<212> TYPE: DNA
<213> ORGANISM: Artificial Sequence
<220> FEATURE:
<223> OTHER INFORMATION: Synthetic primer

<400> SEQUENCE: 20
cagtcaggaa tgacgttcca ggcg                                         24

<210> SEQ ID NO 21
<211> LENGTH: 18
<212> TYPE: DNA
<213> ORGANISM: Artificial Sequence
<220> FEATURE:
<223> OTHER INFORMATION: Synthetic primer

<400> SEQUENCE: 21
tcccctgtga ccgagttc                                                18

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
ccaatcggct ctccttactc                                              20

<210> SEQ ID NO 23
<211> LENGTH: 20
<212> TYPE: DNA
```

```
<213> ORGANISM: Artificial Sequence
<220> FEATURE:
<223> OTHER INFORMATION: Synthetic primer

<400> SEQUENCE: 23
acaggccctc agttcatttc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
gtggacgcct ggaacgtcat                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
cttgaggact ccagggcagt                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
tgcggttatt tcgattgtca                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
agacaaatcg ctccaccaac                                              20

<210> SEQ ID NO 28
<211> LENGTH: 59
<212> TYPE: PRT
<213> ORGANISM: Hirudo medicinalis

<400> SEQUENCE: 28
```

Asp Cys Tyr Glu Asp Trp Ser Arg Cys Thr Pro Gly Thr Ser Phe Leu
1               5                   10                  15

Thr Gly Ile Leu Trp Lys Asp Cys His Ser Arg Cys Lys Glu Leu Gly
            20                  25                  30

His Arg Gly Gly Arg Cys Val Asp Ser Pro Ser Lys His Cys Pro Gly
        35                  40                  45

Val Leu Lys Asn Asn Lys Gln Cys His Cys Tyr
    50                  55

```
<210> SEQ ID NO 29
<211> LENGTH: 56
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(22)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (28)..(36)
<223> OTHER INFORMATION: Xaa can be any naturally occurring amino acid
<220> FEATURE:
<221> NAME/KEY: misc_feature
<222> LOCATION: (38)..(44)
<223> OTHER INFORMATION: Xaa can be any naturally occurring amino acid
<220> FEATURE:
<221> NAME/KEY: misc_feature
<222> LOCATION: (46)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid

<400> SEQUENCE: 29

Cys Xaa Xaa Xaa Xaa Xaa Xaa Cys Xaa Xaa Xaa Xaa Xaa Xaa Xaa Xaa
1               5                   10                  15

Xaa Xaa Xaa Xaa Xaa Xaa Cys Xaa Xaa Xaa Cys Xaa Xaa Xaa Xaa Xaa
            20                  25                  30

Xaa Xaa Xaa Xaa Cys Xaa Xaa Xaa Xaa Xaa Xaa Xaa Cys Xaa Xaa Xaa
        35                  40                  45

Xaa Xaa Xaa Xaa Xaa Cys Xaa Cys
    50                  55

<210> SEQ ID NO 30
<211> LENGTH: 57
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(22)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (28)..(37)
<223> OTHER INFORMATION: Xaa can be any naturally occurring amino acid
<220> FEATURE:
<221> NAME/KEY: misc_feature
<222> LOCATION: (39)..(44)
<223> OTHER INFORMATION: Xaa can be any naturally occurring amino acid
<220> FEATURE:
<221> NAME/KEY: misc_feature
<222> LOCATION: (46)..(54)
<223> OTHER INFORMATION: Xaa can be any naturally occurring amino acid
<220> FEATURE:
<221> NAME/KEY: misc_feature
<222> LOCATION: (56)..(56)
```

-continued

<223> OTHER INFORMATION: Xaa can be any naturally occurring amino acid

<400> SEQUENCE: 30

```
Cys Xaa Xaa Xaa Xaa Xaa Xaa Cys Xaa Xaa Xaa Xaa Xaa Xaa Xaa
1               5                   10                  15

Xaa Xaa Xaa Xaa Xaa Xaa Cys Xaa Xaa Xaa Cys Xaa Xaa Xaa Xaa
            20                  25                  30

Xaa Xaa Xaa Xaa Xaa Cys Xaa Xaa Xaa Xaa Xaa Cys Xaa Xaa Xaa
        35                  40                  45

Xaa Xaa Xaa Xaa Xaa Xaa Cys Xaa Cys
        50                  55
```

<210> SEQ ID NO 31
<211> LENGTH: 58
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(22)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (28)..(37)
<223> OTHER INFORMATION: Xaa can be any naturally occurring amino acid
<220> FEATURE:
<221> NAME/KEY: misc_feature
<222> LOCATION: (39)..(44)
<223> OTHER INFORMATION: Xaa can be any naturally occurring amino acid
<220> FEATURE:
<221> NAME/KEY: misc_feature
<222> LOCATION: (46)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid

<400> SEQUENCE: 31

```
Cys Xaa Xaa Xaa Xaa Xaa Xaa Cys Xaa Xaa Xaa Xaa Xaa Xaa Xaa
1               5                   10                  15

Xaa Xaa Xaa Xaa Xaa Xaa Cys Xaa Xaa Xaa Cys Xaa Xaa Xaa Xaa
            20                  25                  30

Xaa Xaa Xaa Xaa Xaa Cys Xaa Xaa Xaa Xaa Xaa Cys Xaa Xaa Xaa
        35                  40                  45

Xaa Xaa Xaa Xaa Xaa Xaa Xaa Cys Xaa Cys
        50                  55
```

<210> SEQ ID NO 32
<211> LENGTH: 56
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(22)

```
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (28)..(36)
<223> OTHER INFORMATION: Xaa can be any naturally occurring amino acid
<220> FEATURE:
<221> NAME/KEY: misc_feature
<222> LOCATION: (38)..(44)
<223> OTHER INFORMATION: Xaa can be any naturally occurring amino acid
<220> FEATURE:
<221> NAME/KEY: misc_feature
<222> LOCATION: (46)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid

<400> SEQUENCE: 32

Cys Xaa Xaa Xaa Xaa Xaa Xaa Cys Xaa Xaa Xaa Xaa Xaa Xaa Xaa
1               5                   10                  15

Xaa Xaa Xaa Xaa Xaa Xaa Cys Xaa Xaa Cys Xaa Xaa Xaa Xaa Xaa
            20                  25                  30

Xaa Xaa Xaa Xaa Cys Xaa Xaa Xaa Xaa Xaa Xaa Cys Xaa Xaa Xaa
        35                  40                  45

Xaa Xaa Xaa Xaa Xaa Cys Xaa Cys
    50                  55

<210> SEQ ID NO 33
<211> LENGTH: 57
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(22)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (28)..(36)
<223> OTHER INFORMATION: Xaa can be any naturally occurring amino acid
<220> FEATURE:
<221> NAME/KEY: misc_feature
<222> LOCATION: (38)..(44)
<223> OTHER INFORMATION: Xaa can be any naturally occurring amino acid
<220> FEATURE:
<221> NAME/KEY: misc_feature
<222> LOCATION: (46)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid

<400> SEQUENCE: 33

Cys Xaa Xaa Xaa Xaa Xaa Xaa Cys Xaa Xaa Xaa Xaa Xaa Xaa Xaa
1               5                   10                  15

Xaa Xaa Xaa Xaa Xaa Xaa Xaa Cys Xaa Xaa Cys Xaa Xaa Xaa Xaa
            20                  25                  30
```

```
Xaa Xaa Xaa Xaa Cys Xaa Xaa Xaa Xaa Xaa Xaa Cys Xaa Xaa Xaa
        35                  40                  45

Xaa Xaa Xaa Xaa Xaa Xaa Cys Xaa Cys
    50                  55
```

<210> SEQ ID NO 34
<211> LENGTH: 57
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(22)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (28)..(36)
<223> OTHER INFORMATION: Xaa can be any naturally occurring amino acid
<220> FEATURE:
<221> NAME/KEY: misc_feature
<222> LOCATION: (38)..(43)
<223> OTHER INFORMATION: Xaa can be any naturally occurring amino acid
<220> FEATURE:
<221> NAME/KEY: misc_feature
<222> LOCATION: (45)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid

<400> SEQUENCE: 34

```
Cys Xaa Xaa Xaa Xaa Xaa Xaa Cys Xaa Xaa Xaa Xaa Xaa Xaa Xaa
1               5                   10                  15

Xaa Xaa Xaa Xaa Xaa Xaa Cys Xaa Xaa Xaa Cys Xaa Xaa Xaa Xaa
            20                  25                  30

Xaa Xaa Xaa Xaa Cys Xaa Xaa Xaa Xaa Xaa Xaa Cys Xaa Xaa Xaa
        35                  40                  45

Xaa Xaa Xaa Xaa Xaa Xaa Cys Xaa Cys
    50                  55
```

<210> SEQ ID NO 35
<211> LENGTH: 23
<212> TYPE: DNA
<213> ORGANISM: Artificial Sequence
<220> FEATURE:
<223> OTHER INFORMATION: Synthetic primer

<400> SEQUENCE: 35
ctcttctcaa caagttgctc tgc                                    23

<210> SEQ ID NO 36
<211> LENGTH: 26
<212> TYPE: DNA
<213> ORGANISM: Artificial Sequence
<220> FEATURE:
<223> OTHER INFORMATION: Synthetic primer

<400> SEQUENCE: 36
cagcaagtac gagaggcaaa aggaca                                 26

```
<210> SEQ ID NO 37
<211> LENGTH: 75
<212> TYPE: PRT
<213> ORGANISM: Theromyzon tessulatum

<400> SEQUENCE: 37

Gly Cys Phe Glu Asp Trp Ser Arg Cys Ser Pro Ser Thr Ser Arg Gly
1               5                   10                  15

Thr Gly Val Leu Trp Arg Asp Cys Asp Ser Tyr Cys Lys Val Cys Phe
            20                  25                  30

Lys Ala Asp Arg Gly Glu Cys Phe Asp Ser Pro Ser Leu Asn Cys Pro
        35                  40                  45

Gln Arg Leu Pro Asn Asn Lys Gln Cys Arg Cys Ile Asn Ala Arg Thr
    50                  55                  60

Ala Lys Asp Asn Arg Asn Pro Thr Cys Trp Ala
65                  70                  75

<210> SEQ ID NO 38
<211> LENGTH: 75
<212> TYPE: PRT
<213> ORGANISM: Hirudo medicinalis

<400> SEQUENCE: 38

Gly Cys Phe Glu Asp Trp Ser Arg Cys Ser Pro Ser Thr Ala Ser Ala
1               5                   10                  15

Thr Gly Val Leu Trp Arg Ser Cys Asp Ser Tyr Cys Lys Val Cys Phe
            20                  25                  30

Lys Ala Asp Arg Gly Glu Cys Tyr Asp Ser Pro Ser Leu Asn Cys Pro
        35                  40                  45

His Arg Leu Pro Asn Asn Lys Gln Cys Arg Cys Ile Asn Ala Arg Thr
    50                  55                  60

Ala Lys Asp Asn Arg Asn Pro Thr Cys Trp Ala
65                  70                  75
```